US010548619B2

(12) United States Patent
Wallace et al.

(10) Patent No.: US 10,548,619 B2
(45) Date of Patent: Feb. 4, 2020

(54) SELECTIVE SPINAL TISSUE REMOVAL APPARATUS AND METHOD

(71) Applicant: Michael P. Wallace, Pleasanton, CA (US)

(72) Inventors: Michael P. Wallace, Pleasanton, CA (US); Roy Leguidleguid, Union City, CA (US); Gary Heit, LaHonda, CA (US)

(73) Assignee: Michael P. Wallace, Pleasanton, CA (US)

( * ) Notice: Subject to any disclaimer, the term of this patent is extended or adjusted under 35 U.S.C. 154(b) by 1049 days.

(21) Appl. No.: 14/877,825

(22) Filed: Oct. 7, 2015

(65) Prior Publication Data

US 2016/0022283 A1 Jan. 28, 2016

Related U.S. Application Data

(63) Continuation-in-part of application No. 13/544,111, filed on Jul. 9, 2012, now abandoned.

(51) Int. Cl.
| *A61B 17/16* | (2006.01) |
| *A61B 17/32* | (2006.01) |
| *A61B 17/00* | (2006.01) |
| *A61B 17/3207* | (2006.01) |

(52) U.S. Cl.
CPC ...... *A61B 17/1671* (2013.01); *A61B 17/1631* (2013.01); *A61B 17/1642* (2013.01); *A61B 17/32002* (2013.01); *A61B 2017/00331* (2013.01); *A61B 2017/32007* (2017.08); *A61B 2017/320074* (2017.08); *A61B 2017/320791* (2013.01)

(58) Field of Classification Search
CPC ............ A61B 17/1615; A61B 17/1624; A61B 17/1631; A61B 17/1642; A61B 17/1659; A61B 17/1671
See application file for complete search history.

(56) References Cited

U.S. PATENT DOCUMENTS

| 620,356 A | 2/1899 | Pratt |
| 2,406,600 A | 8/1946 | Forestiere |
| 3,746,220 A | 7/1973 | Harbaugh |
| 4,243,040 A | 1/1981 | Beecher |
| 4,362,161 A | 12/1982 | Reimels et al. |
| 5,330,480 A | 7/1994 | Meloul et al. |
| 5,364,345 A | 11/1994 | Lowery et al. |
| 5,371,429 A | 12/1994 | Manna |
| 5,392,970 A | 2/1995 | Orosei |
| 6,568,572 B1 | 5/2003 | Smith |
| 6,569,181 B1 | 5/2003 | Burns |
| 6,730,104 B1 | 5/2004 | Sepetka et al. |
| 6,740,090 B1 | 5/2004 | Cragg et al. |
| 7,189,240 B1 | 3/2007 | Dek el |
| 7,621,870 B2 | 11/2009 | Berrada et al. |

(Continued)

FOREIGN PATENT DOCUMENTS

WO WO 2011/091383 A1 7/2011

*Primary Examiner* — Si Ming Ku
(74) *Attorney, Agent, or Firm* — Shay Glenn LLP

(57) ABSTRACT

Method and devices for cutting and removing a portion of a tissue composition which includes cancellous bone which is directly or indirectly impinging on a neural structure of the spine by creating channels through the tissue structure and then removing the detached tissue.

12 Claims, 29 Drawing Sheets

(56) References Cited

U.S. PATENT DOCUMENTS

| | | |
|---|---|---|
| 7,641,658 B2 * | 1/2010 | Shaolian ............ A61B 17/1617 |
| | | 606/170 |
| 7,766,921 B2 | 8/2010 | Sepetka et al. |
| 7,780,696 B2 | 8/2010 | Daniel et al. |
| 7,887,538 B2 | 2/2011 | Bleich et al. |
| 7,896,879 B2 | 3/2011 | Solsberg et al. |
| 8,932,319 B2 | 1/2015 | Martin et al. |
| 2003/0176884 A1 | 9/2003 | Berrada et al. |
| 2004/0260333 A1 | 12/2004 | Dubrul et al. |
| 2005/0283166 A1 | 12/2005 | Greenhalgh |
| 2006/0004367 A1 * | 1/2006 | Alamin ............. A61B 17/7064 |
| | | 606/74 |
| 2008/0208255 A1 | 8/2008 | Siegal |
| 2008/0300591 A1 | 12/2008 | Darian et al. |
| 2009/0024118 A1 | 1/2009 | Vercellotti et al. |
| 2010/0249815 A1 | 9/2010 | Jantzen et al. |
| 2011/0251615 A1 | 10/2011 | Truckai et al. |
| 2014/0012261 A1 | 1/2014 | Nita et al. |
| 2015/0005781 A1 | 1/2015 | Lund-Clausen et al. |

\* cited by examiner

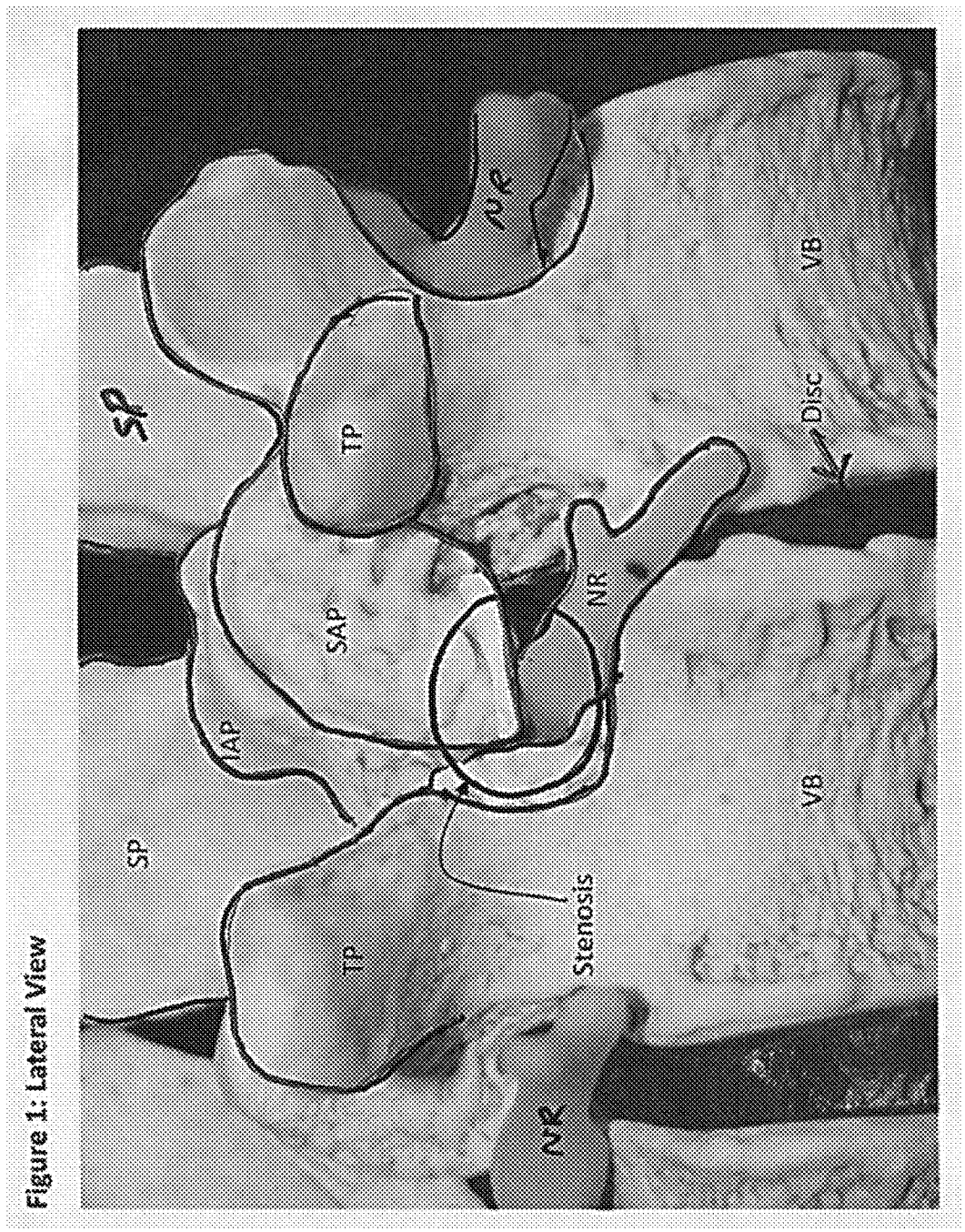

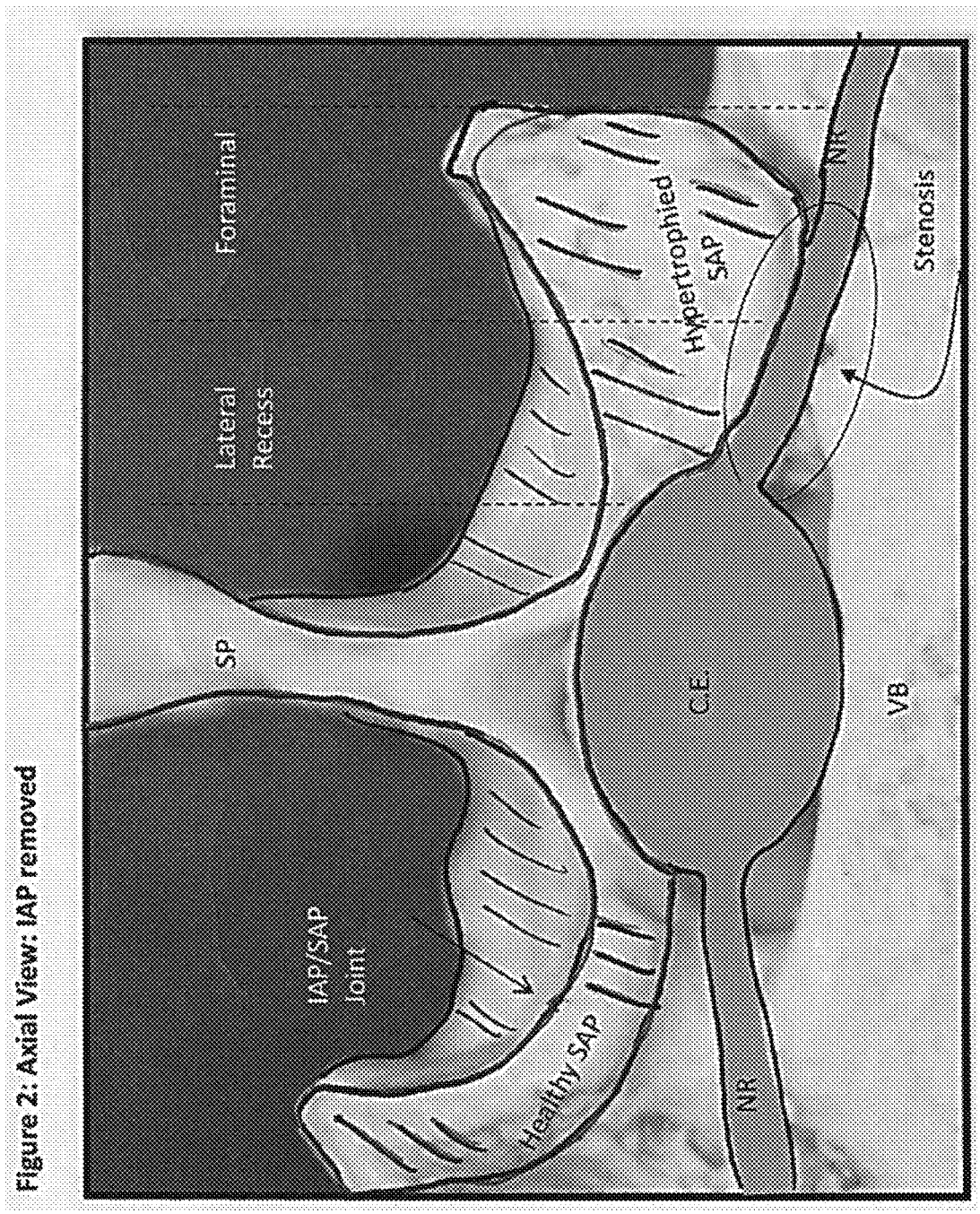

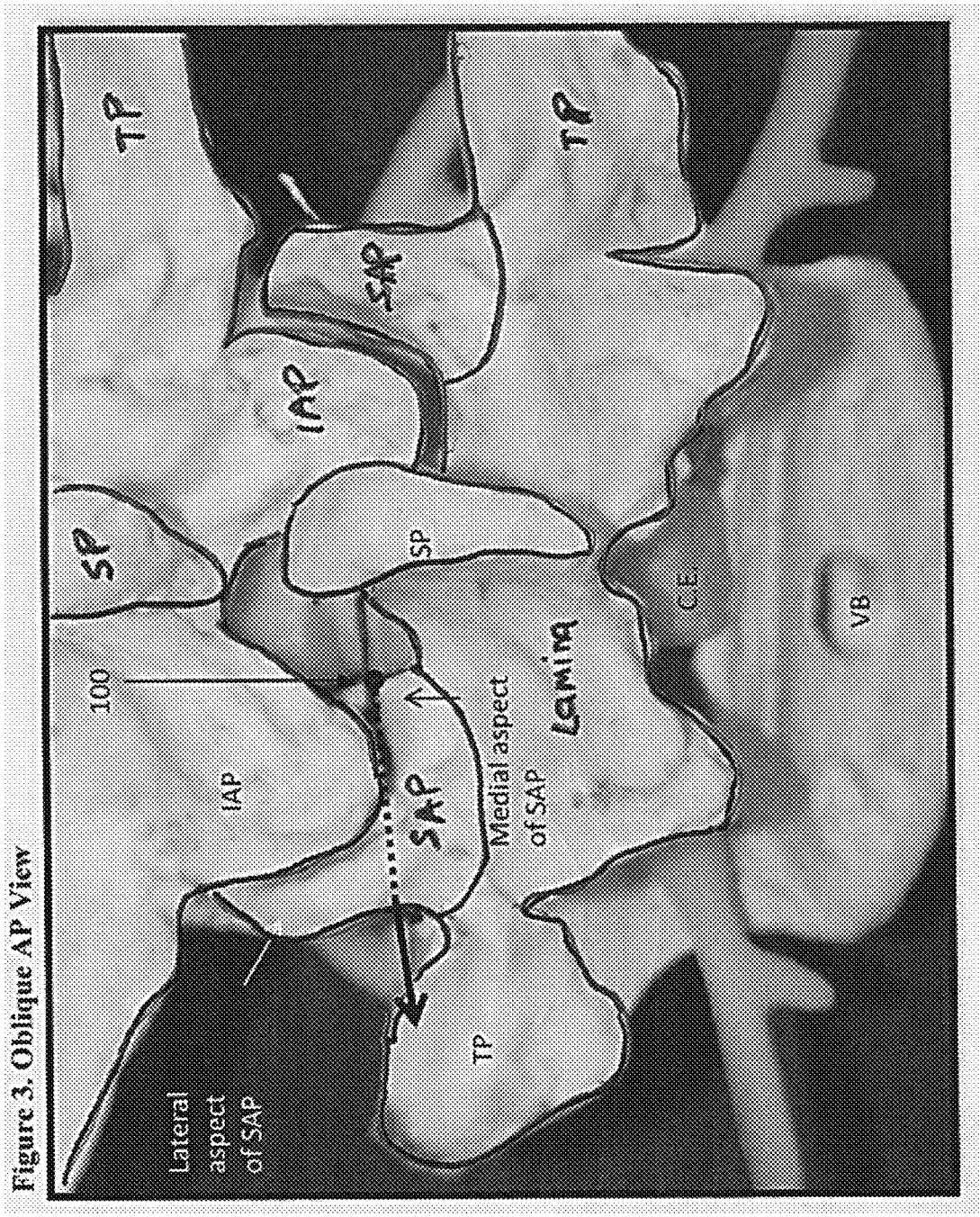

Figure 4. Oblique Lateral View
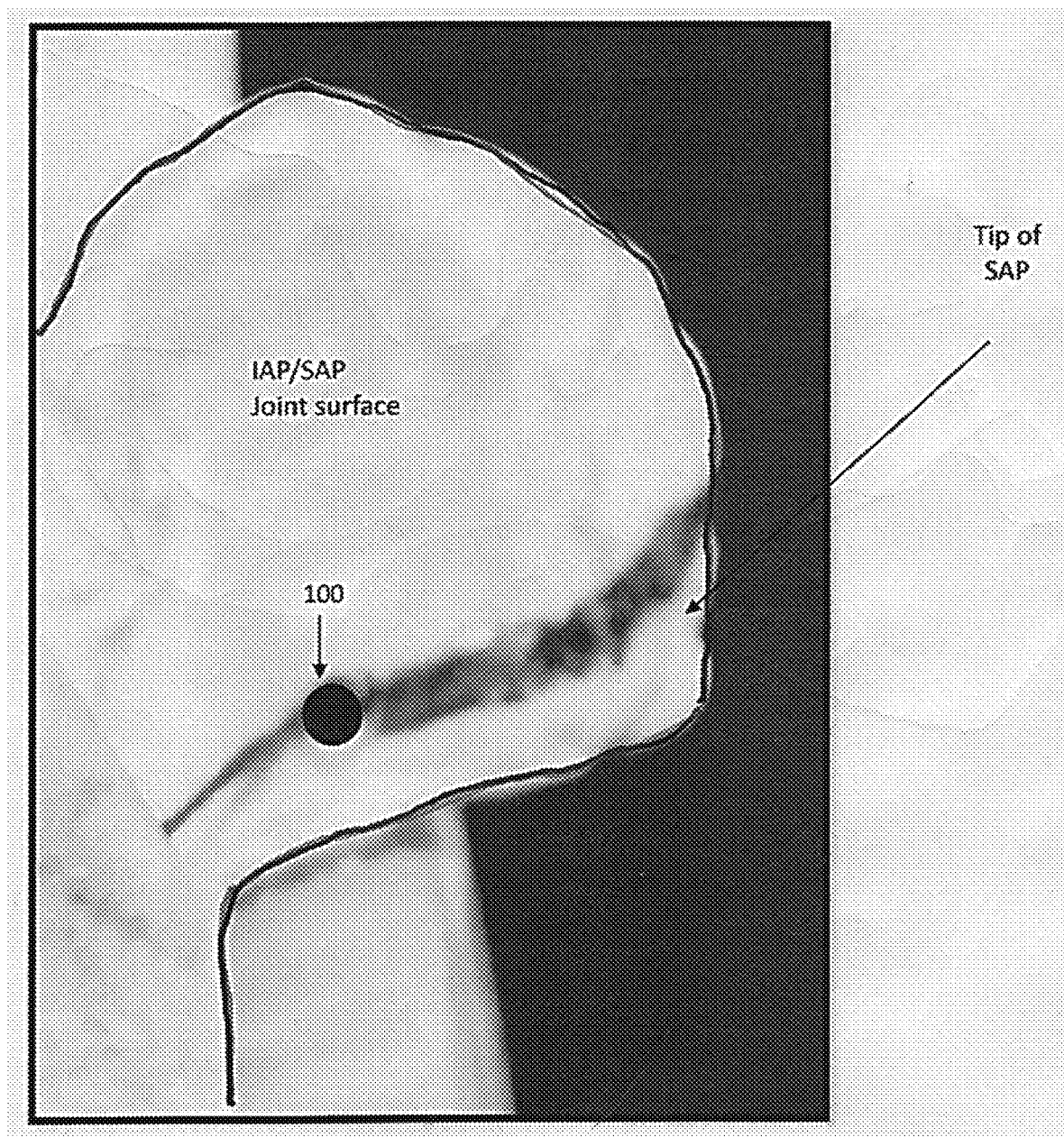

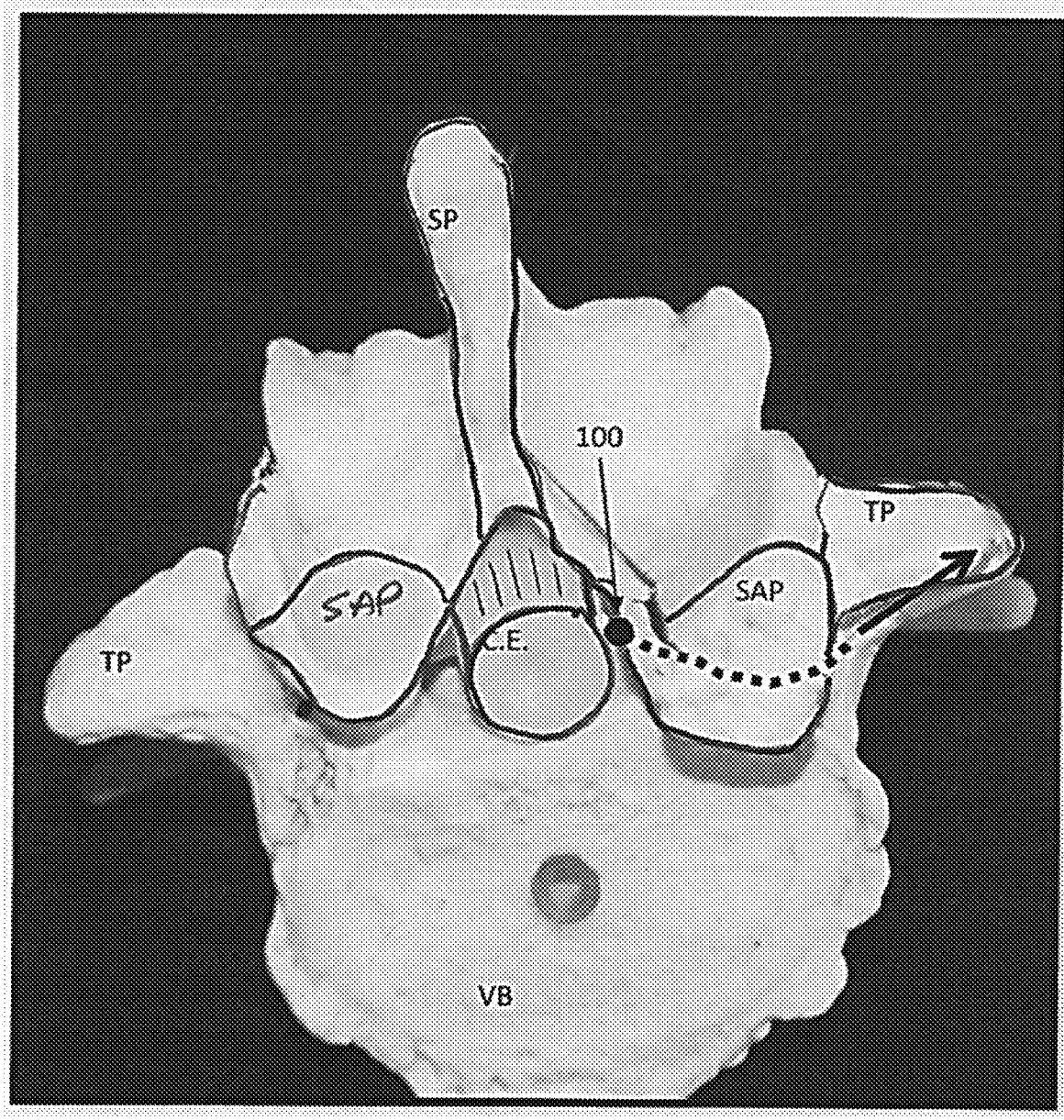

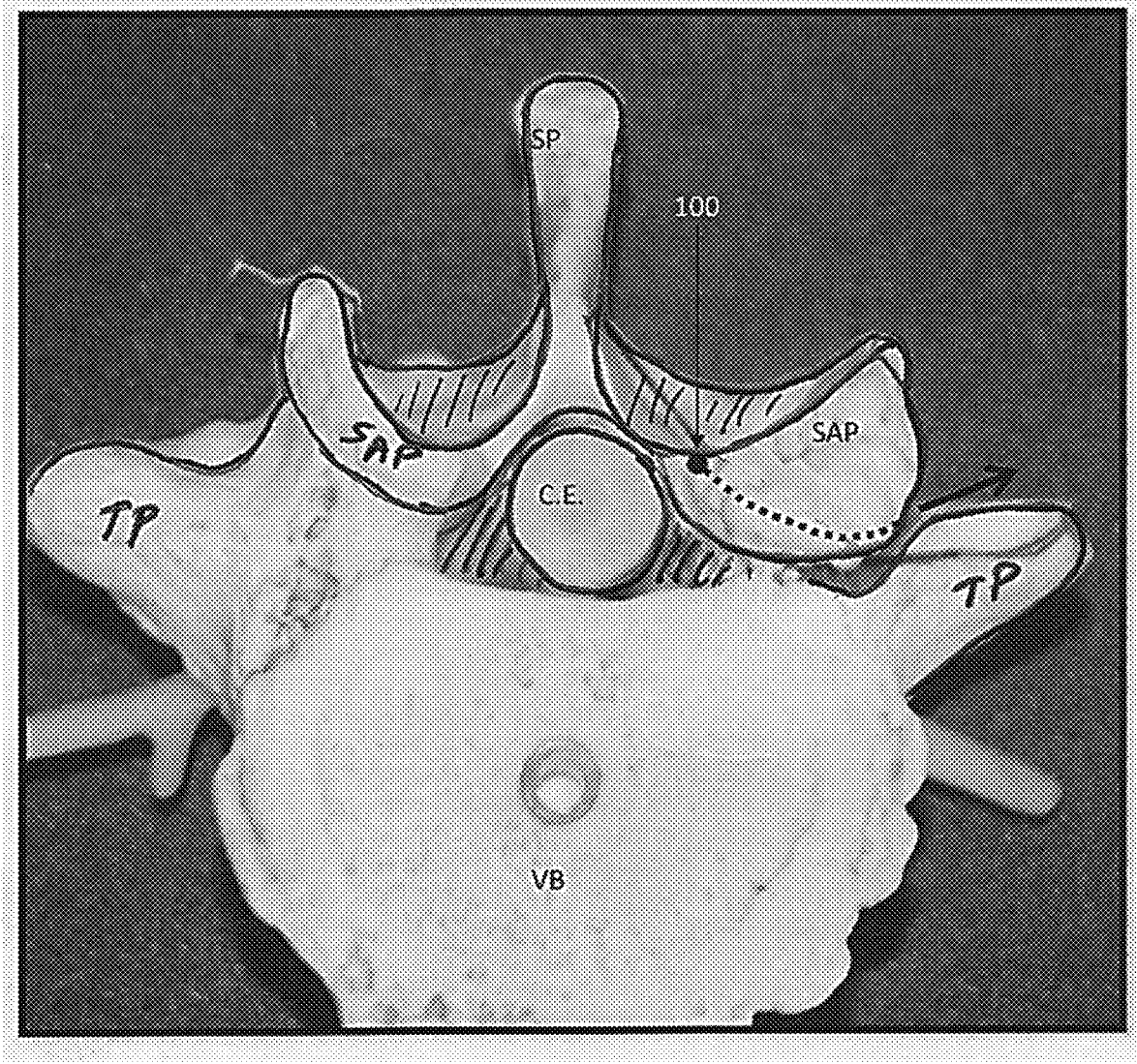

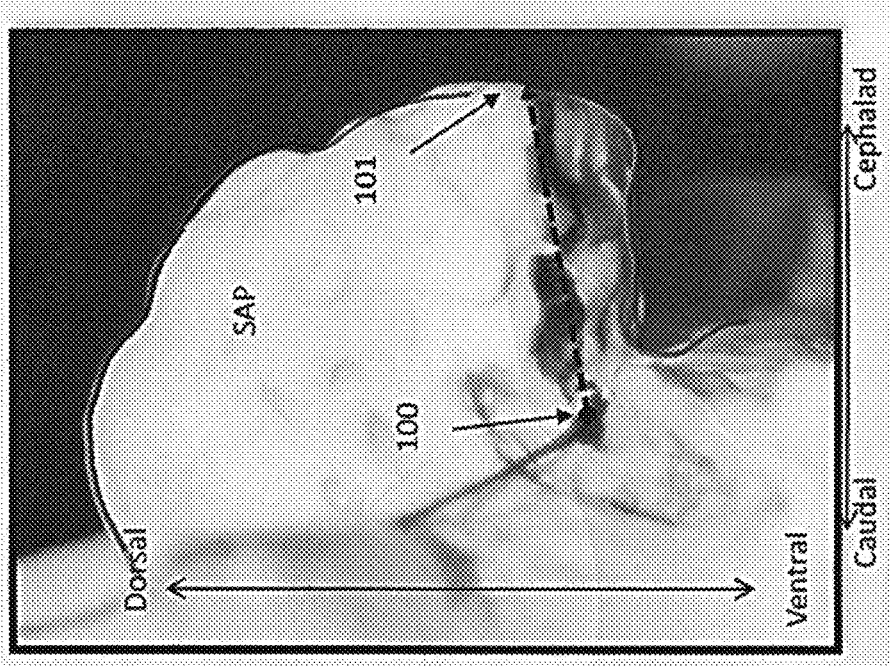
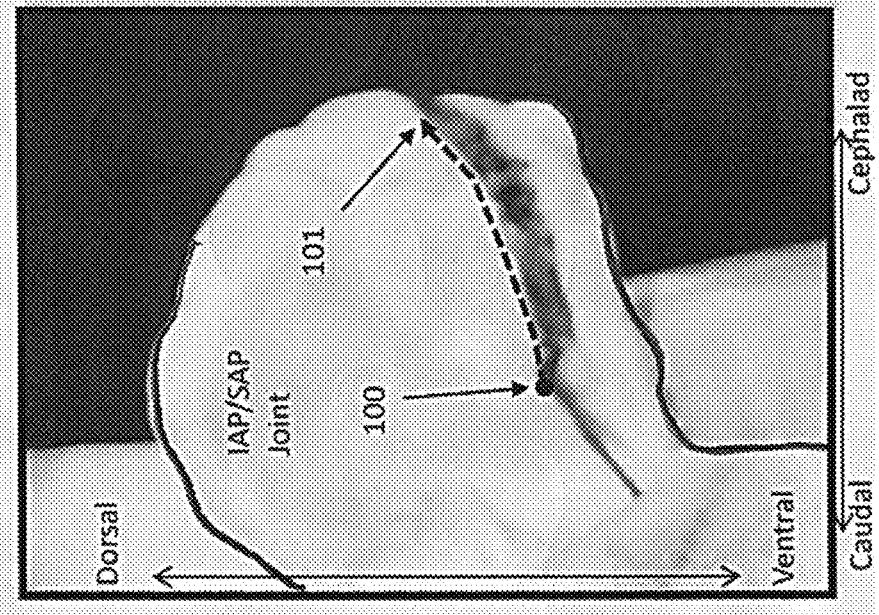

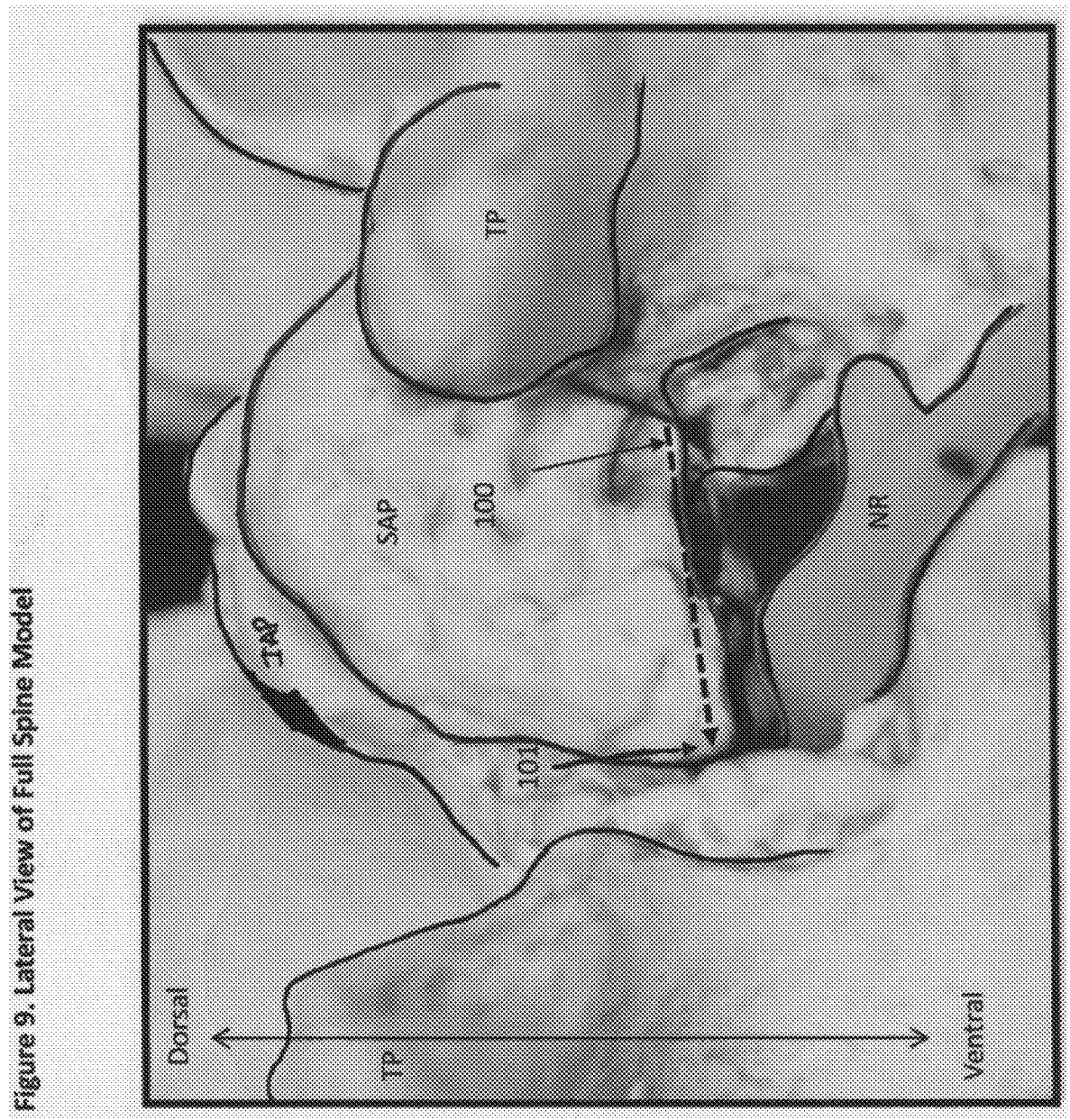

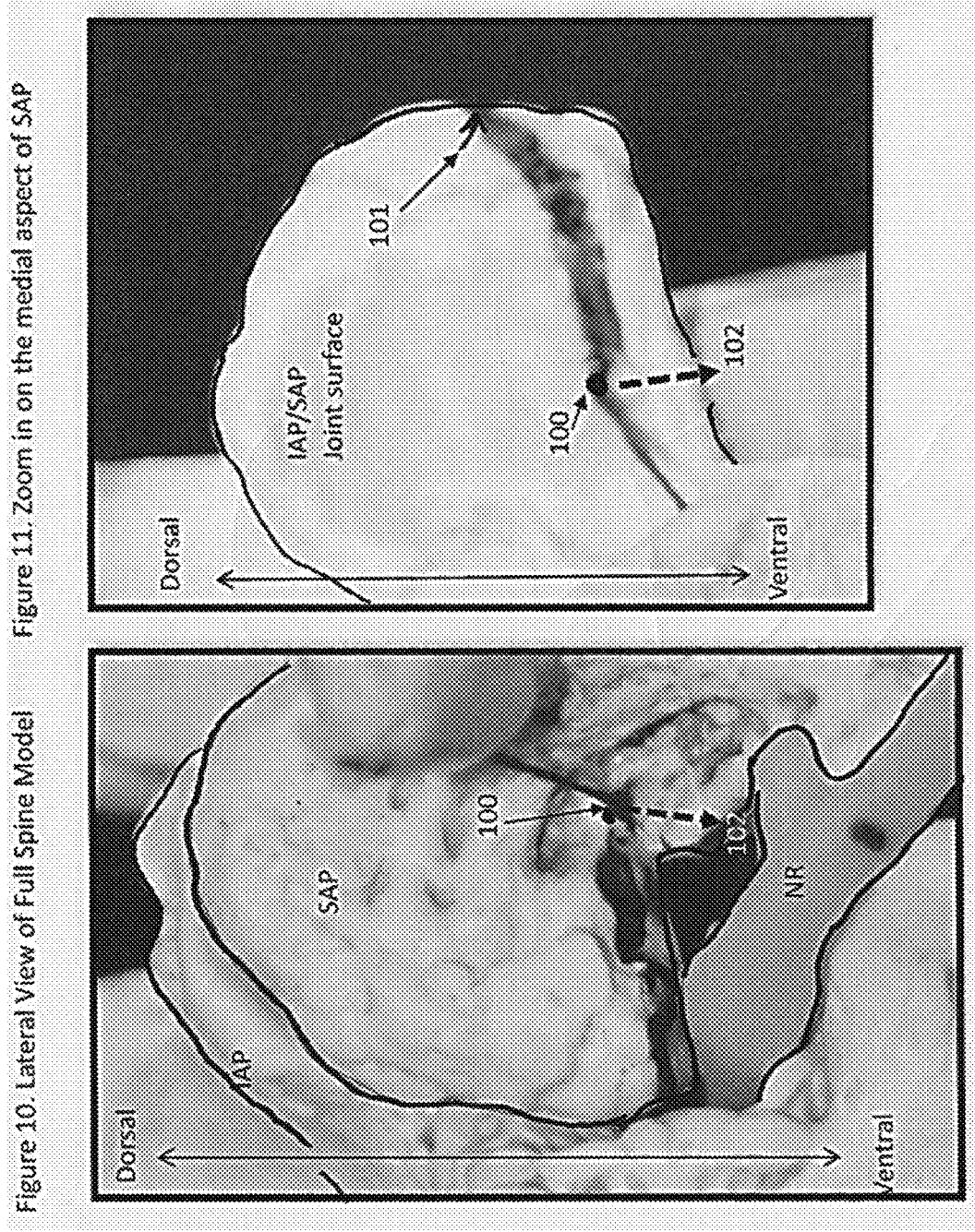

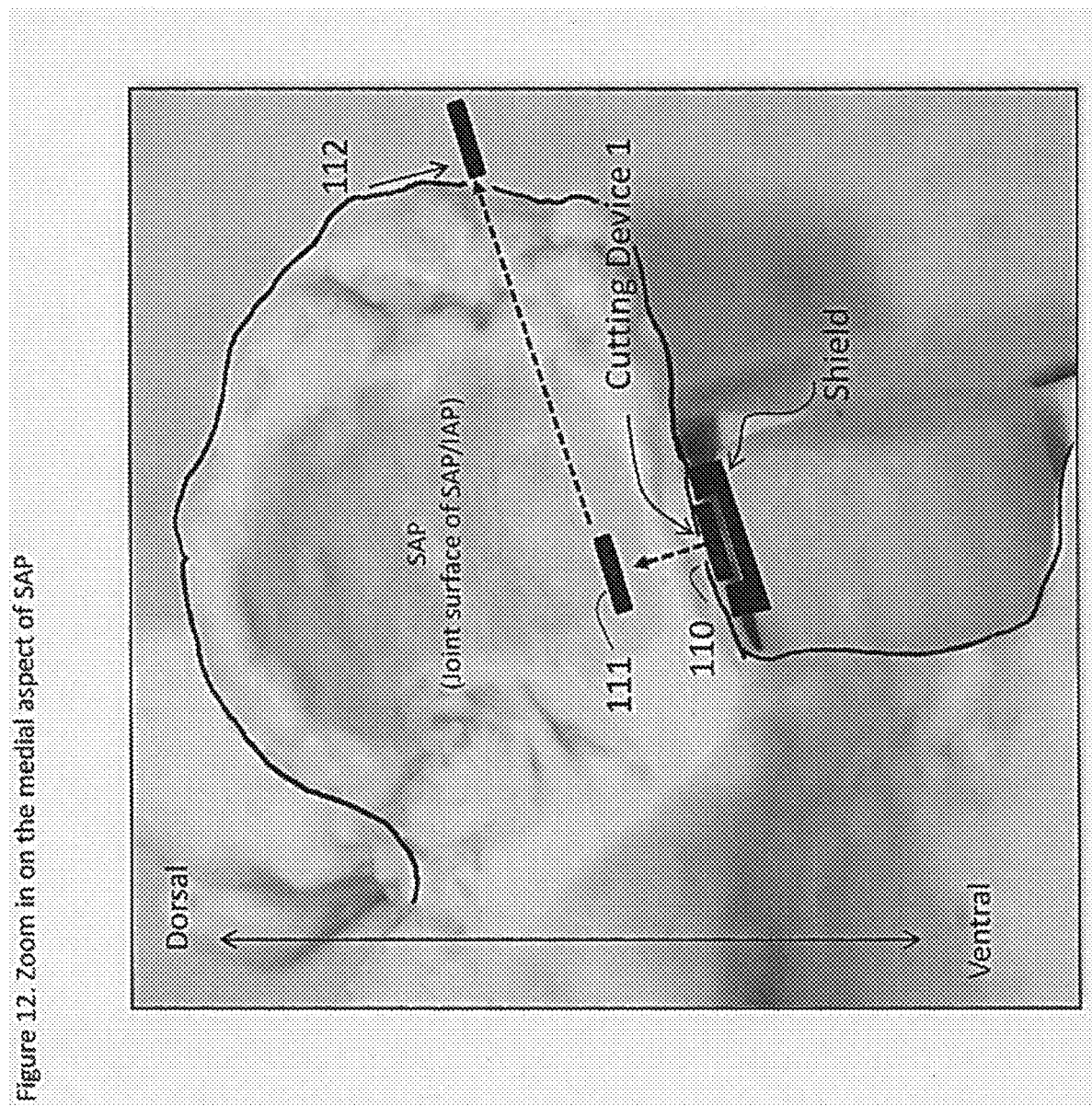

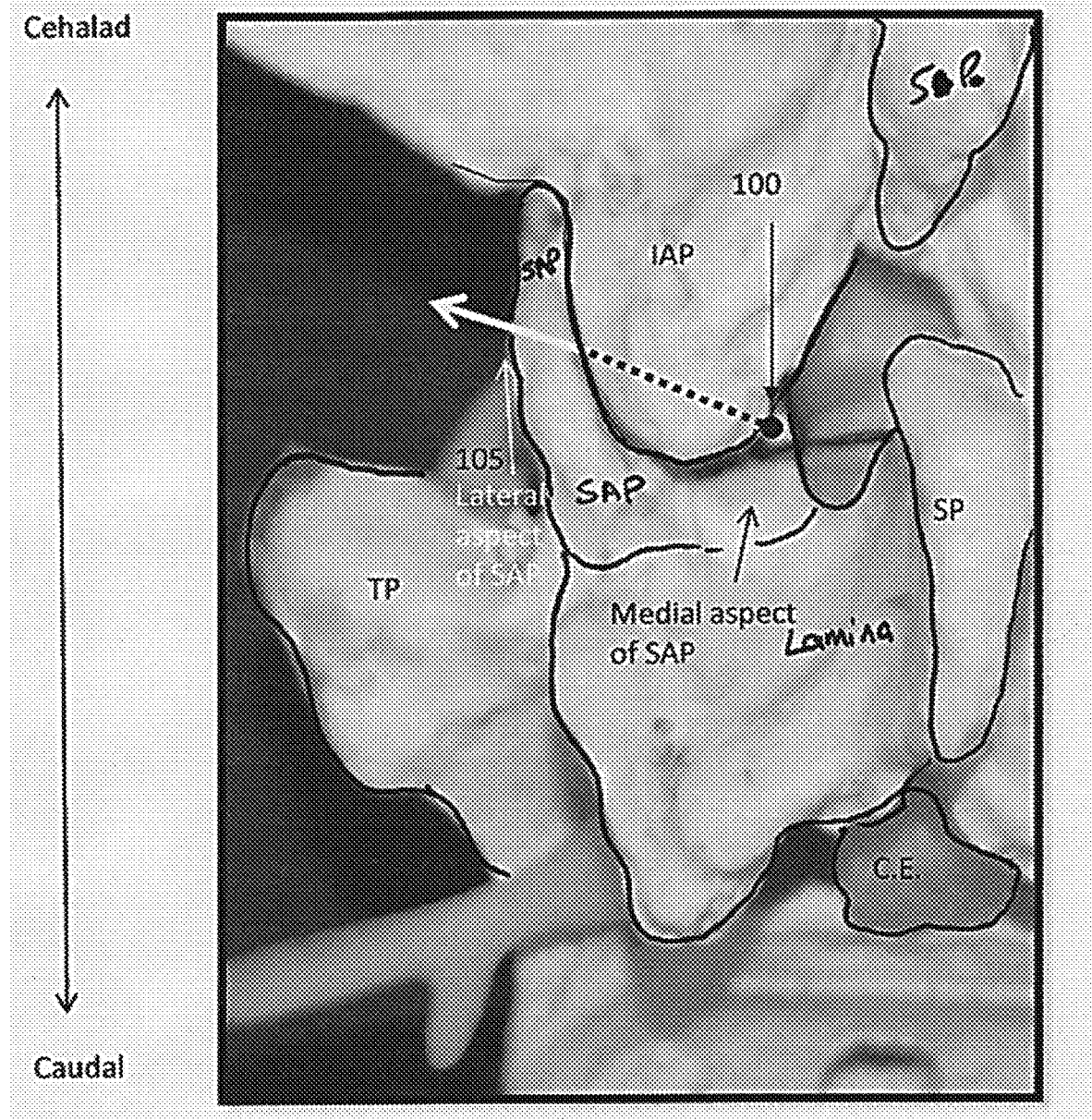

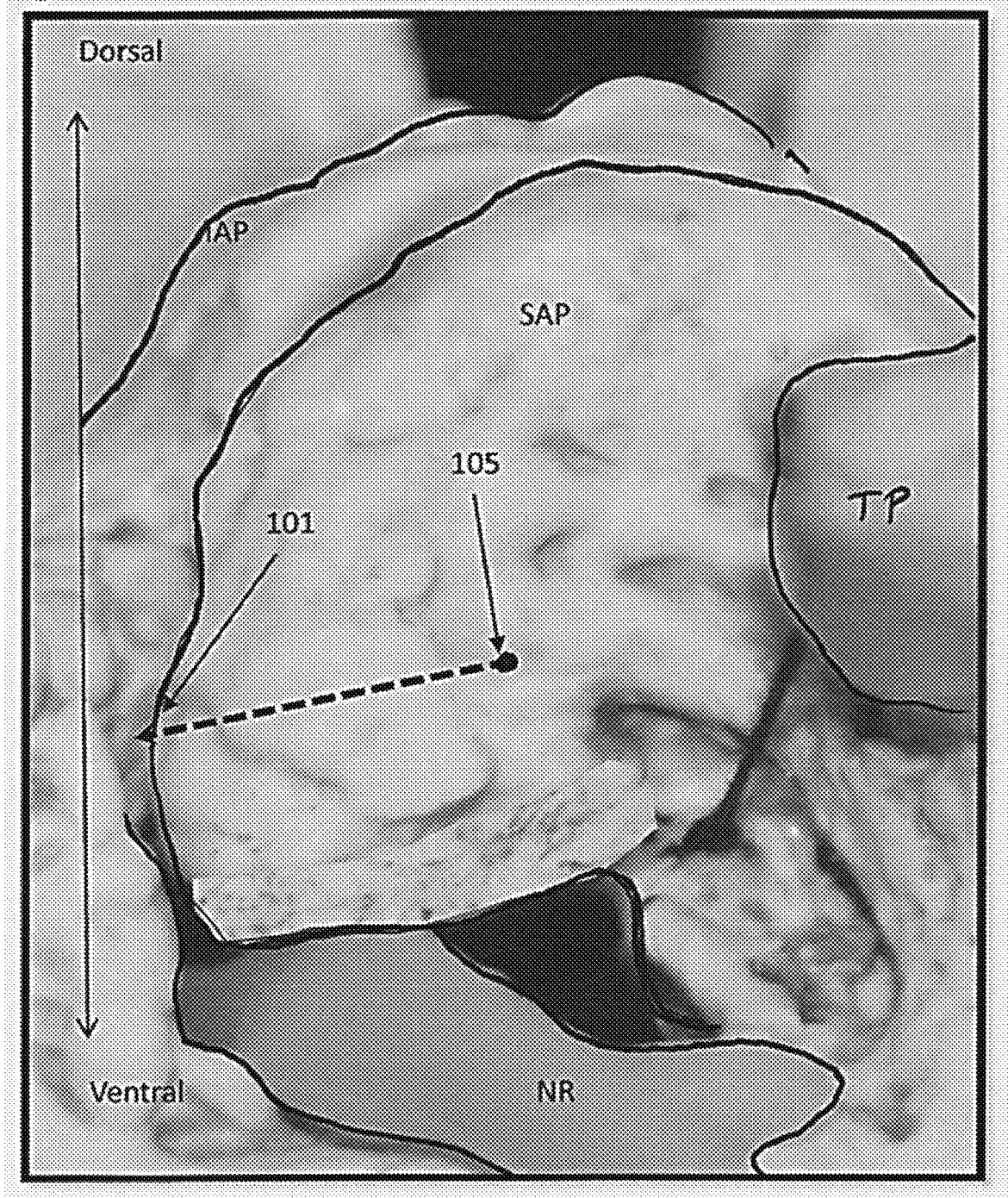

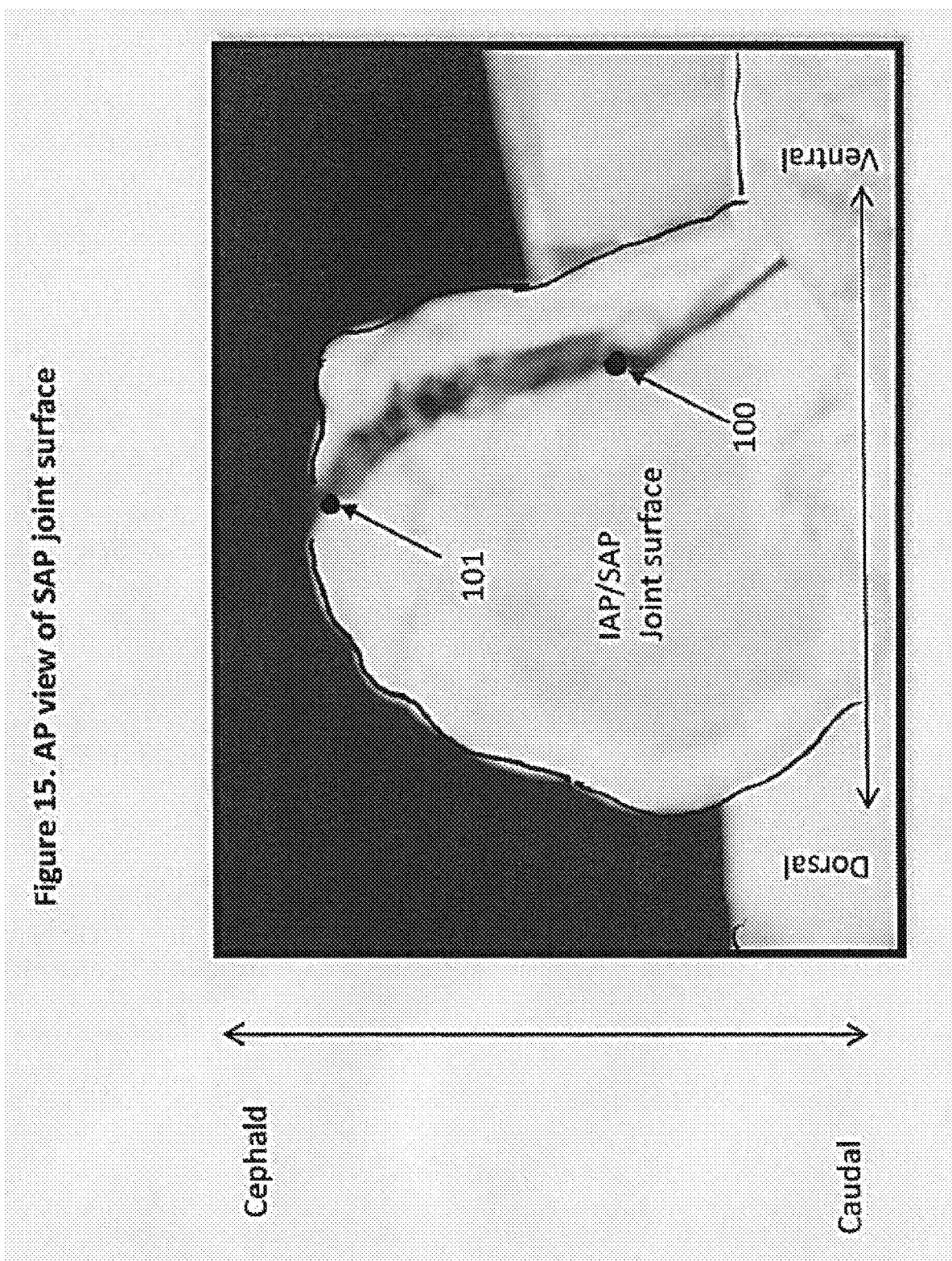

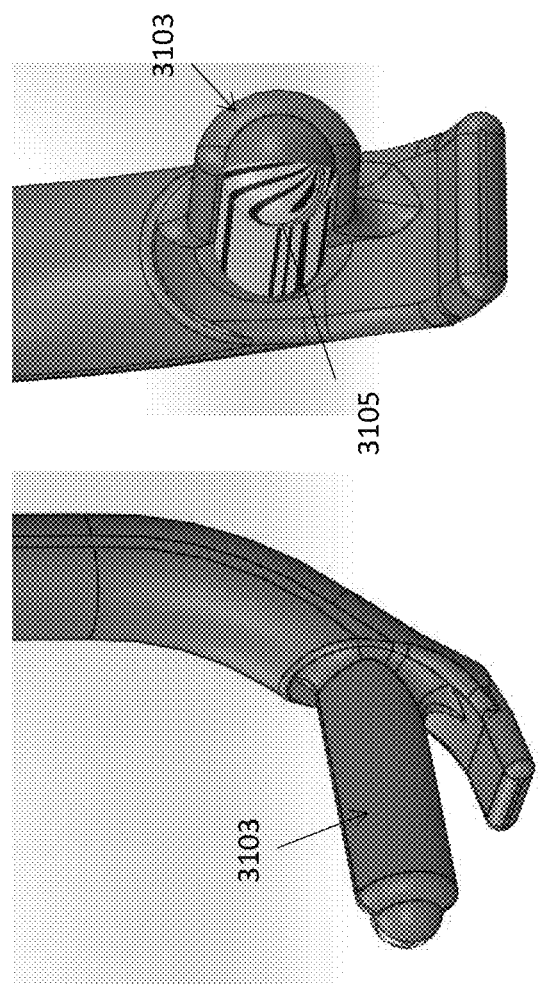
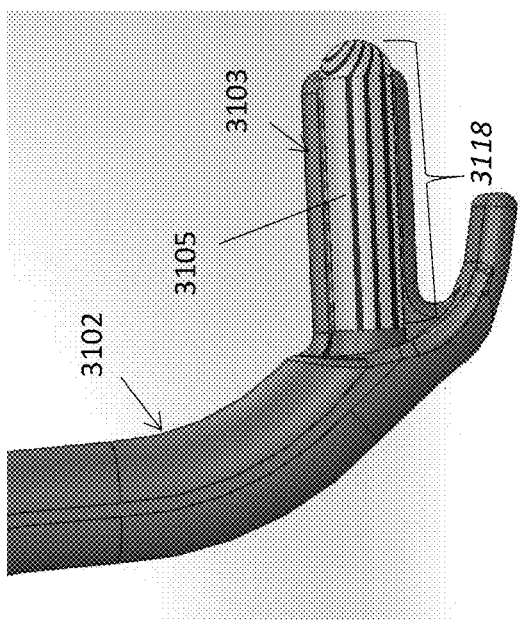
FIG. 31A  FIG. 31B  FIG. 31C

SELECTIVE SPINAL TISSUE REMOVAL APPARATUS AND METHOD

CROSS REFERENCE TO RELATED APPLICATIONS

This application is a continuation-in-part of U.S. patent application Ser. No. 13/544,111, filed Jul. 9, 2012, titled "ULTRASOUND ENHANCED SELECTIVE TISSUE REMOVAL METHOD AND APPARATUS," Publication No. US 2014-0012261 A1, which is herein incorporated by reference in its entirety.

This is related to provisional application No. 61/518,082, filed Apr. 29, 2011.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND OF THE INVENTION

1. Field of the Invention

The present invention relates to methods and apparatuses for removing and remodeling lateral recess and neural foramina enlargement of the spine. More specifically, it relates to removal of tissue or bone from the lateral recess, neural foramina and central spinal canal areas using ultrasound or other tools.

2. Description of the Prior Art

Pathological compression of spinal neural and neurovascular structures most commonly results from a degenerative, age-related process, increasing in prevalence and severity in elderly populations, with potential congenital anatomic components, that result in back, radicular extremity pain and both neurological (e.g., sensory) and mechanical (e.g., motor) dysfunction. Prevalence is also influenced by congenital spinal anatomy. This disease progression leads to increased neural irritation, neural and neurovascular impingement, and ischemia, and is frequently accompanied by progressively increased pain, often in conjunction with reflex, sensory and motor neurological deficits.

In the United States, spinal stenosis occurs with an incidence of between 4 percent and 6 percent of adults 50 years of age or older, and is the most frequent reason cited for back surgery in patients 60 years of age and older. Spinal stenosis often includes neural and/or neurovascular impingement, which may occur in the central spinal canal, the lateral recesses of the spinal canal, or in the spinal neural foramina. The most common causes of neural compression within the spine are spinal disc disease (collapse, bulging, herniation); ligamentum flavum buckling, thickening and/or hypertrophy; zygapophysial (facet) joint hypertrophy; osteophyte formation; and spondylolisthesis. Disease progression increases neural irritation, impingement, and ischemia, and is frequently accompanied by progressively increased pain, often in conjunction with reflex, sensory and motor neurological changes (e.g., deficits).

Current surgical treatments for spinal stenosis include laminectomy (usually partial, but sometimes complete), laminotomy and/or facetectomy (usually partial, but sometimes complete), with or without fusion. While standard surgical procedures (e.g., spinal decompressions) lead to improvements in symptoms for 6 months or more in approximately 60% of cases, there is an unacceptable incidence of long-term complications and morbidity: approximately 40% of patients do not obtain sustained improvement with current surgical decompressions.

There are several tools that facilitate surgical access to the areas of the spine where neural impingement is likely to occur, in order to allow the surgeon to decompress the impinged neural structures through the removal of vertebral lamina, ligamentum flavum, facet complex, bone spurs, and/or intervertebral disc material. These surgical resections are frequently (i.e., occurs in 15% to 20% of cases) accompanied by fusion (arthrodesis). Spinal arthrodesis is performed to fuse adjacent vertebrae and prevent movement of these structures in relation to each other. The fusion is commonly a treatment for pain of presumed disc or facet joint origin; for severe spondylolisthesis; for presumed spinal instability; and for spines that have been rendered "unstable" by the surgical decompression procedures, as described above. The definition of "spinal instability" remains controversial in current literature.

Spinal arthrodesis may be achieved through various surgical techniques. Biocompatible metallic hardware and/or autograft or allograft bone is commonly placed (e.g., secured) anteriorly and/or posteriorly in the vertebral column in order to achieve surgical fusion. These materials are secured along and between the vertebral bodies (to restore vertebral height and replace disk material) and/or within the posterior elements, typically with pedicle screw fixation. Autograft bone is often harvested from the patient's iliac crest. Cadaveric allograft is frequently cut in disc shaped sections of long bones for replacement of the intervertebral discs in the fusion procedure.

Critics have frequently stated that while discectomy and fusion procedures frequently improve symptoms of neural impingement in the short term, both are highly destructive procedures that diminish spinal function, drastically disrupt normal anatomy, and increase long-term morbidity above levels seen in untreated patients.

The high morbidity associated with discectomy may be due to several factors. First, discectomy reduces disc height, causing increased pressure on facet joints. This stress leads to facet arthritis and facet joint hypertrophy, which then causes further neural compression. The surgically-imposed reduction in disc height also may lead to neuroforaminal stenosis, as the vertebral pedicles, which form the superior and inferior borders of the neural foramina, become closer to one another. The loss of disc height also creates ligament laxity, which may lead to spondylolisthesis, spinal instability or osteophyte or "bone spur" formation, as it has been hypothesized that ligaments may calcify in their attempt to become more "bone-like". In addition, discectomy frequently leads to an incised and further compromised disc annulus. This frequently leads to recurrent herniation of nuclear material through the surgically created or expanded annular opening. It may also cause further buckling of the ligamentum flavum. The high morbidity associated with fusion is related to several factors. First, extensive hardware implantation may lead to complications due to breakage, loosening, nerve injury, infection, rejection, or scar tissue formation. In addition, autograft bone donor sites (typically the patient's iliac crest) are a frequent source of complaints, such as infection, deformity, and protracted pain. Perhaps the most important reason for the long-term morbidity caused by spinal fusion is the loss of mobility in the fused segment of the spine. Not only do immobile vertebral segments lead to functional limitations, but they also cause increased stress on adjacent vertebral structures, thereby frequently accelerating the degeneration of other discs, joints, bone and other soft tissue structures within the spine.

Recently, less invasive, percutaneous approaches to spinal discectomy and fusion have been tried with some success. While these less invasive techniques offer advantages, such as a quicker recovery and less tissue destruction during the procedure, the new procedures do not diminish the fact that even less invasive spinal discectomy or fusion techniques are inherently destructive procedures that accelerate the onset of acquired spinal stenosis and result in severe long-term consequences.

Additional less invasive treatments of neural impingement within the spine include percutaneous removal of nuclear disc material and procedures that decrease the size and volume of the disc through the creation of thermal disc injury. While these percutaneous procedures may produce less tissue injury, their efficacy remains unproven.

Even more recently, attempts have been made to replace pathological discs with prosthetic materials. While prosthetic disc replacement is a restorative procedure, it is a highly invasive and complex surgery. Any synthetic lumbar disc will be required to withstand tremendous mechanical stresses and may require several years of development. Current synthetic disc designs cannot achieve the longevity desired. Further, synthetic discs may not be an appropriate therapeutic approach to a severely degenerative spine, where profound facet arthropathy and other changes are likely to increase the complexity of disc replacement. Like most prosthetic joints, it is likely that synthetic discs will have a limited lifespan and that there will be continued need for minimally invasive techniques that delay the need for disc replacement.

Even if prosthetic discs become a viable solution, the prosthetic discs will be very difficult to revise for patients. The prosthesis will, therefore, be best avoided in many cases. A simpler, less invasive approach to restoration of functional spinal anatomy would play an important role in the treatment of neural impingent in the spine. The artificial discs in U.S. clinical trials, as with any first generation prosthesis, are bound to fail in many cases, and will be very difficult to revise for patients. The prostheses will, therefore, be best avoided, in many cases. Lumbar prosthetic discs are available in several countries worldwide.

In view of the aforementioned limitations of prior art techniques for treating neural and neurovascular impingement in the spine, it would be desirable to provide methods and apparatus for selective surgical removal of tissue that reduce or overcome these limitations.

The present invention provides a method that allows for the removal of the offending tissue, primarily bony and soft tissue, in any joint in the body without causing iatrogenic instability to the patient. One method described herein addresses the treatment of a specific joint/neural impingement in the spine known as spinal stenosis. The methods and apparatus described herein can be applied to a variety of nerve stenosis areas in the body, including the hand, wrist, foot, knee, shoulder, neck etc.

Traditional surgical techniques for the treatment of spinal stenosis involve the removal of all the offending tissue pressing on the cauda equina (C.E) or the nerve root (bone & ligament). This common surgical technique uses tools such as the rongeur or rotary drill (i.e., Midas Rex by Medtronic) and can often lead to the inadvertent removal of more of the facet joint than is desired while trying to decompress the neural structures adequately. When more tissue (or the joint) is removed than desired to decompress the nerve, the risk of causing iatrogenic instability (physician caused) of the spine is increased, thereby producing a new set of problems for the patient. The technique of the present invention allows removal of the offending tissue while maintaining the majority of the facet joint, reducing the risk of causing near-term or long-term joint stability issues, yet directly removing most of the hard-to-reach tissue that is pressing on the neural structures in the lateral recess and foramen.

At least two commercially used MIS procedures have been developed to address the limitations of traditional spinal decompression surgery techniques, but the challenges of direct visualization or a visualization surrogate are still required to avoid inadvertent damage to the neural structure. One MIS procedure involves the use of endoscopy for visualization (Richard Wolf, Yeung Endoscopic Decompression Procedure) and adds significant complexity and learning curve to the procedure due to the limited field of view and challenges in differentiating tissue types (i.e. nerve versus ligament) associated with small endoscopes in tight spaces such as the spinal foramen. Another technique described in the literature suggests the use of mechanical devices such as drills, manually operated rasps, and power-actuated reciprocating saws to remove tissue only after confirming the location of the tissue removal tools through a surrogate visualization system such as neuro stimulation free running and triggered EMG. By using stimulation and triggered EMG, the surgeon can confirm that the neural structures are not going to be in the pathway of the tissue removal techniques. However, the use of visualization surrogates (such as triggered EMG) adds complexity and cost to the procedure thereby posing commercial impediments for surgeon and hospital adoption of the procedure.

The present invention addresses the iatrogenic instability limitations of the common 'invasive' surgical procedures and many of the practical adoption challenges associated with the known MIS procedures. In particular, the invention avoids the need for complicated visualization methods (endoscopy) or visualization surrogates (stimulation/EMG) by ensuring that the trajectory of the cutting devices are always dorsai to the exiting nerve root, and/or that the cutting devices used in this procedure only cut hard tissue (i.e. bone or calcified ligament or disc) and do not cut soft tissue such as nerve, dura, blood vessels or muscle.

SUMMARY OF THE DISCLOSURE

The present invention provides a method of cutting and removing a portion of a tissue structure which is directly or indirectly impinging on a neural structure. According to one variation of the methods described herein, a first channel is created through the majority of the tissue structure's cross section, and then through the first channel, a second channel is created orthogonal to the first channel where the second channel extends from the first channel to an edge of the tissue structure to define a tissue portion for removal. The tissue portion is then detached from the tissue structure.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1 illustrates a lateral view of a model that demonstrates lateral stenosis. The model shows the stenosis between the ventral aspect of the SAP and the dorsal aspect of the disc and vertebral body (VB). The stenosis is demonstrated by the nerve root being compressed by the ventral aspect of the SAP.

FIG. 2 illustrates a model showing lateral recess and foraminal stenosis.

FIGS. 3 and 4 are two views illustrating a first step of a tissue removal method according to a first embodiment of the present invention through the use of a model, where the trajectory of the medial to lateral bore hole is created.

FIGS. 5 and 6 are two other views illustrating the first step of a tissue removal method according to the first embodiment of the present invention through the use of a model, where a medial to lateral bore hole is created.

FIGS. 7 and 8 are two views illustrating a second step of a tissue removal method according to the first embodiment of the present invention through the use of a model, the ventral aspect of SAP.

FIG. 9 is a lateral view of the model in FIGS. 7 and 8.

FIGS. 10 and 11 are two views illustrating a third step of a tissue removal method according to the first embodiment through the use of a model, the removal of a slice of tissue.

FIG. 12 illustrates a tissue removal method according to a second embodiment of the present invention through the use of a model.

FIGS. 13 and 14 illustrate a tissue removal method according to a third embodiment of the present invention through the use of a model.

FIG. 15 illustrates a tissue removal method according to a fourth embodiment of the present invention through the use of a model.

FIGS. 31A-31C illustrate another example of a deployable rotary device having a side cutter in side, side perspective and front perspective views, respectively.

DETAILED DESCRIPTION

Figure 16:
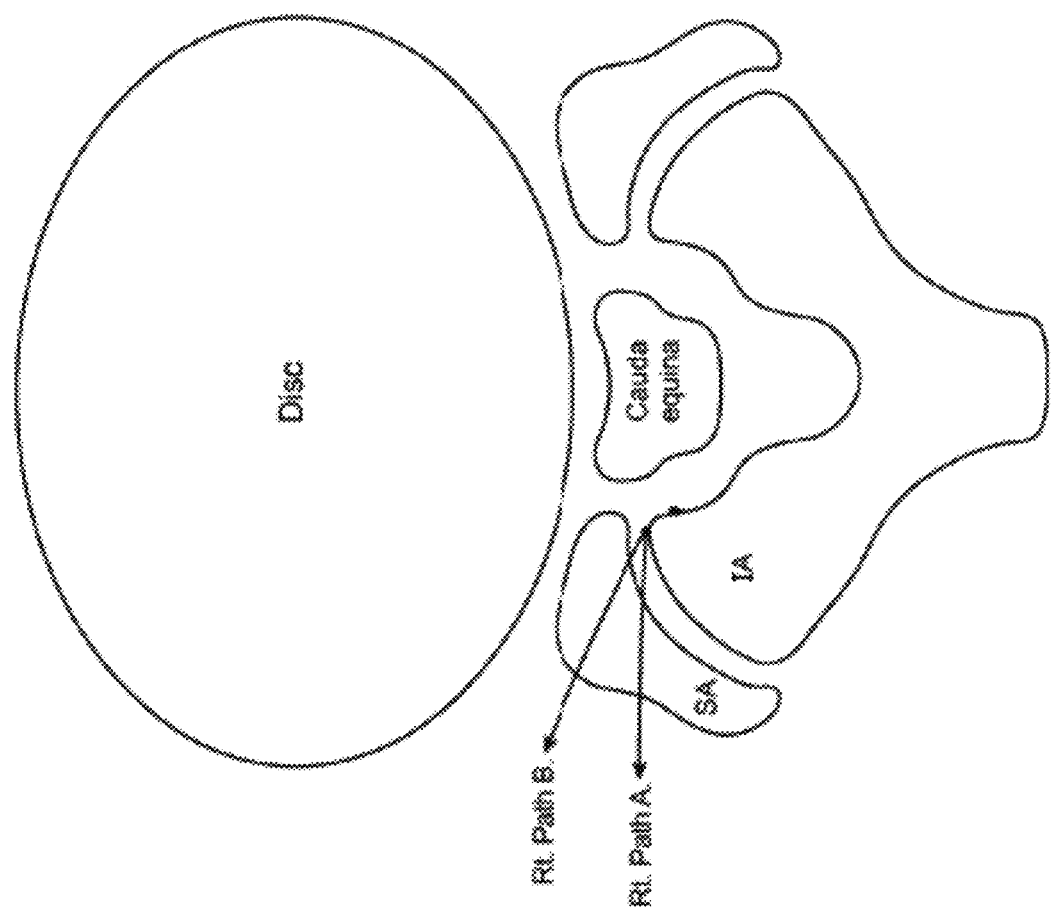
FIG. 16 is a schematic of a lumbar spine showing the two possible trajectories of the burr hole through the SAP: either the straight trajectory (Rt. Path A) or the curved trajectory (Rt. Path B).

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

As used herein, the following acronyms shall mean the following terms:

TP: transverse process SP: superior process VB: vertebral body SAP: superior articular process IAP: inferior articular process NR: nerve root CE: cauda equine The lumbar spine typically has five vertebrae (L1-L5). Each vertebra is stacked on top of the other, and between each vertebra is a gel-like cushion called a disc (intervertebral disc). The discs help to absorb pressure, distribute stress, and keep the vertebrae from grinding against each other. The joints in the spine are commonly called facet joints. Other names for these joints are Zygapophyseal or Apophyseal Joints. Each vertebra has two sets of facet joints (left and right side). One pair faces upward (superior articular facet: SAP) and one pair faces downward (inferior articular facet: IAP). Facet joints are hinge-like, and link the vertebrae together. They are located at the back of the spine (posterior). In the lumbar spine, the neural structures consist of the cauda equine, which is located in the central canal between the anteriorly located vertebral body and the posterior structures like the lamina and spinous process. The cauda equina consists of the lumbar nerve roots protected by a dural sheath, known as the dura. Between each vertebral level is a left and right neural foramen for which the respective left and right lumbar nerve root exits. It is these nerve roots or a portion of the cauda equina that becomes compressed when spinal stenosis forms.

FIG. 1 illustrates a model that demonstrates lateral stenosis of the lumbar spine. One form of spinal stenosis can occur from the tip of the SAP pinching on the exiting nerve root, as seen in FIG. 1. There are other forms of neural impingements in the lumbar spine and are often referred to as the following: central stenosis of the CE, lateral recess stenosis of the CE, traversing nerve root in the gutters of the canal, and foraminal stenosis which usually involves stenosis of the exiting nerve root.

FIG. 2 illustrates a model that demonstrates lateral recess stenosis and foraminal stenosis of the lumbar spine.

FIG. 2 shows a hypertrophied or enlarged SAP on one side of the lumbar spine which is compressing the shoulder of the NR and the lateral aspect of the CE (known as lateral recess stenosis) and the exiting nerve root (known as foraminal stenosis).

FIG. 2 clearly shows the three areas of stenosis. Patients with spinal stenosis have a range of neurological pain symptoms including back pain and pain extending into their buttocks, hip and/or legs. This pain is produced by narrowing of the central canal, lateral recess and/or foraminal area of the lumbar spine. When these areas of the spine are narrowed the cauda equina and/or exiting nerve roots can become compressed and cause pain. To relieve pain in these patients, it is important to remove the tissue (bone from the SAP and IAP) and ligaments, including the ligamentum flavum that is pressing on the nerve. However, if too much of the SAP or IAP is removed during the surgery then the facet joint will no longer be a stable functional joint and can cause other pain issues for the patient (known as iatrogenic or surgeon caused spinal instability). Therefore, it is desirable to selectively remove the minimal amount of tissue (bone and/or ligament) necessary to relieve pressure on the neural structures without removing too much facet joint and causing iatrogenic instability The present invention involves selectively removing a portion of the ventral most aspect of the facet joint without causing iatrogenic instability. This method involves targeting the removal of part of the SAP and/or IAP including any attached ligament. The SAP and IAP are the two primary boney structures that are impinging on the cauda equine in the lateral recess or the nerve root(s) located in either the lateral recess or foramen.

Access to the targeted area of the spine can be achieved through traditionally invasive exposures, minimally invasive exposures and/or percutaneous techniques. In all three types of exposures the patient would be positioned in a supine position, face down on the surgical table or on their side. The surgeon's initial incision would be on the posterior or posterior/lateral side of the patient. If traditionally invasive surgical exposures are employed, soft tissue dissection would be achieved through direct visualization such as surgeon's eyes, loops and/or microscope until the lamina would be located. Traditional surgical retractors would be used to retract the dissected soft tissue. For minimally invasive approaches micro-retractors such as the McCullough retractors or rigid or expandable tubular retractors can be used to maintain exposure to the targeted area allowing for introducing of necessary tools. In general, the incision size is smaller than the invasive approaches and often involves techniques to dissect rather than cut any parspinous muscles exposed during the dissection. The surgeon's eyes, loops, microscope or endoscope could be used to achieve direct visualization of the targeted area of the spine with minimally invasive techniques. Alternatively, for percutaneous approaches, defined as any skin exposure less than 14 mm in diameter, endoscopic, fluoroscopy and/or electrical stimulation with EMG feedback techniques would be used to achieve access.

Once access is achieved to the targeted location of the spine, FIGS. 3 and 4 illustrate a first step of a first embodiment of a tissue removal method of the present invention: the creation of a medial to lateral burr hole to treat lateral recess and foraminal stenosis in the spine. From a typical mid-line approach, a point 100 is located by the surgeon somewhere along the medial/cephalad aspect of the SAP. Cephalad is defined as "towards the head of the patient", while "caudal" is defined as "away from the head of the patient". One specific location may include (but is not limited to) the most medial intersection point of the IAP and the SAP (shown as point 100 on FIGS. 3 and 4). After this starting point is located, a tool (such as a drill, a specialized cutting device shown in FIG. 17, or any head-on cutting tool) is used to drill from the point 100 and then directed laterally either on a curved or straight trajectory. Alternatively, it may be desirable to initiate the burr hole starting point 100 on the medial aspect of the IAP rather than the SAP (not shown) or a more dorsal position on the SAP/IAP (not shown). While positioning the burr hole starting at a more dorsal point on SAP or IAP will point may result in removing more of the ventral part of the facet joint (IAP/SAP) by cutting out a larger slice of bone and/or tissue. A more dorsal cutting position for point 100 on FIG. 7 would, it also reduces the chance of inadvertently hitting the exiting nerve root as the cutting tool would also be more dorsal to the plane of the exiting nerve root. Also, a more dorsal position of the starting burr hole related to point 100 in FIG. 17 would reduce the required and the size of the initial mid-line laminectomy/laminotomy used to gain visualization and access to the facet joint (IAP/SAP construct).

FIGS. 5 and 6 are different views illustrating the first step of the tissue removal method of FIGS. 3 and 4, and show a curved trajectory of the burr hole, starting on the medial edge of the SAP and directed towards the lateral aspect of the SAP through a slightly curved trajectory. Alternatively, the burr hole trajectory could be a straight trajectory again starting from the medical aspect of the SAP and then being directed straight to the lateral aspect of the SAP (not shown in FIGS. 5 and 6). Prior to the first step of cutting tissue starting at point 100 in FIG. 7 or at any time during the surgical procedure it may be advantageous to have the targeted spine segment or nearby targeted spine segment(s) in flexion rather than neutral or in extension. By having the targeted spine segment in flexion this allows the offending bone or ligamentous tissue such as the ventral and/or cephalad portions of a hypertrophied SAP and/or IAP to temporarily move away from the neural structures. For example if the surgeon is operating on lumbar level 3-4 and wants to put that segment in flexion they can achieve it in a variety of ways including; positioning the patient belly down with a pillow under their stomach or inserting and deploying a retractor between the level 3-4 spinous process. In this example the level 3-4 SAP tip or cephalad most portion of the SAP as seen in FIG. 9, point 101 will move away from the exiting nerve root (NR). By putting the targeted spine segments in flexion before or during any of the cutting steps described in this application more space is created between the neural structures and the offending tissue causing the stenosis. By creating extra space between the targeted tissues causing the stenosis and neural structures through flexion of the spine segment(s) it makes cutting, shaving, detaching or removing the target tissue easier to achieve without damaging or irritating the neural structures.

FIGS. 7 and 8 illustrate a second step for the tissue removal method of the first embodiment: the ventral aspect of SAP. Using the same or different cutting tool as used for the first step, the cutting tool is positioned through the initial burr hole tract and then a "slice" ventral aspect of the SAP is cut, starting at the caudal location of the SAP where the burr hole was created (point 100) and the cephalad is cut to the desired location (point 101). The trajectory of the cut from point 100 to point 101 can be relatively orthogonal (90 degrees+/−30 degrees) to the burr hold path created in the first step. For the second step cut it may be desirable to cut completely through the SAP (101). The dashed line in FIGS. 7 and 8 demonstrates an example of a cut line. The tissue ventral to the dotted line would be the targeted material to be removed to relieve the stenosis. Alternatively, the direction of the second cut could start more cephalad in the foramen and then the cut could move caudally (not shown). It may also be desirable to make the this second cut just short of the point 101 to avoid the risk of hitting, bumping or irritating the nerve root, NR, with a variety of the cutting methods and/or tools. If the cut is made short of point 101, a curette, Woodson or other stiff tool can be positioned within the cut formed by the second step. Next, the curette, Woodson or other stiff tool can be rotated to fracture the remaining bony connection. Specifically, this technique would result in removing the "slice of tissue" from the ventral aspect of the SAP (area ventral to the dotted line in FIGS. 7 and 8) that is causing the stenosis. Alternatively, an initial burr hole point 100, FIG. 17 could be positioned more cephalad in the foramen and then the direction of the second cut could start from this more cephalad position and the second cut would be directed in a caudal direction along the facet joint (not shown).

FIG. 9 illustrates a similar view as FIGS. 7 and 8, showing the cut from point 100 to point 101. The tissue ventral to the dotted line is known herein as the slice of tissue desired to be removed.

In the third step of the method of the first embodiment, the slice of tissue is removed. This can be accomplished using one of several techniques. In a first technique, a device such as a curette can be placed in the cut line created in the second step, and rotated to snap the piece of bone connecting point 100 to point 102 shown in FIGS. 10 and 11. Point 102 is the most cephalad point of the SAP, or a point near the most cephalad end of the SAP. Other devices, such as a pituitary or other grabbing instruments, could be used to remove the piece of bone and attached joint capsule and/or ligament. Other alternative ways to aid in the removal of the slice involves the use of suction, the use of a hook-shaped or barbed tool to grab the slice and allow the surgeon to pull out. The hooked shaped or barbed tool could grab an edge of the slice or stick into the slice to make the connection more secure prior to removal. An alternative way of removing the slice involves using a cutting/drilling tool to partially drill into the slice to effectively grab or tether the slice and then pull it out of the foramen. Alternatively, a cutting device can be placed near the burr hole 100 created in the first step and then pushed down ventrally towards the cauda equina (point 102), as shown by the dotted line in FIGS. 10 and 11. When appropriate, any grabbing tool, such as an up-biting pituitary, can be used to grab the 'slice' and remove the tissue.

The order of the procedural steps described above as the first, second and third steps can be changed if advantageous. Also, once the ventral aspect of the SAP has been cut and removed per the three steps, it may be desirable to seal the cut surface with bone wax to discourage the long term risk of excessive bone growth in that area as a result of the healing process associated with the newly exposed cancellous bone. Cancellous bone is typically encapsulated by cortical bone. When cancellous bone in the spine is exposed to other tissues, as a result of removing part of the encapsulating cortical bone, the cancellous bone structure may grow in size in an attempt to heal. Therefore, it is important in the region of the spine when cancellous bone is exposed by the surgeon to limit the potential growth of this structure during the healing process by covering the cut surface with bone wax or another moldable or adaptable substance that limits bleeding and future growth of the exposed bone surface. Future growth of boney elements in the spine may in itself create stenosis of the spinal cannula or the nerve root foramen.

FIG. 12 illustrates a tissue removal technique according to a second embodiment of the present invention. Rather than the three-step procedure described above, FIG. 12 describes an alternative procedure for removing tissue from a foramen.

FIG. 12 shows an alternative method which involves inserting a cutting tool with an integrated shield, or separately delivering the shield and subsequently the cutting tool. The shield & cutting tool could be constructed so the cutting tool is offset by 1-15 mm. This system may be constructed so the user can adjust the offset amount (1-15 mm) prior to cutting bone in the patient. In FIG. 12 the tools (cutting tool and shield) are placed dorsal to the dura (on top of) of the cauda equina/nerve root(s) and ventral (below) to the ventral aspect of the SAP. These devices can be inserted on the medial aspect of the SAP (point 110 in FIG. 12) and be deployed in the lateral direction, or they can originate on the lateral aspect of the SAP and be directed medially. The shield can be integrated with the cutting tools or can be separate. If the shield is separate, it would first be positioned in the spine. Once the shield in place, a cutting device would be deployed on the dorsal side of the shield. It may be desirable to have the cutting device be indexed off the shield to avoid migration of the cutting tool. If there is little room for the cutting tool to be deployed between the shield on the dorsal side and the ventral aspect of the SAP on the ventral side, it may be desirable to allow the cutting device to cut head-on and thereby allow it to create its own space while being deployed. Once the tip of the cutting tool is deployed out the neural the device would cut dorsally from point 110 to point 111. Next a cutting device would cut from point 111 to 112 to allow for full resection of the 'slice', shown in FIG. 12 as the area of tissue ventral to the dotted line created by connecting points 111 to 112 and the right of the dashed line created by connecting points 110 to 111. Alternatively, the cutting device shown in FIG. 12 can have an integrated shield (not shown). The integrated shield is similar to the separate shield solution described above, and can direct the device to cut only in targeted directions. In FIG. 12, the shield limits the cutting tool to cutting in the dorsal direction thereby avoiding the neural structures located ventral to the device. Once the cutting tool cuts from point 110 to 111, the shield may be removed or rotated about the cutting tool to allow it to cut bone in the direction of point 112.

FIGS. 13 and 14 illustrate a tissue removal technique according to a third embodiment of the present invention. Rather than the three-step procedure described above, FIGS. 13 and 14 describe an alternative procedure for removing tissue from a foramen. In FIG. 13, the first step involves creating a hole from medial to lateral (point 100 to point 105) through the SAP, and possibly through the ventral aspect of the IAP at a slight cephalad angle. This facilitates focusing the decompression on the tip of the SAP. In the second step (see FIG. 14), a cut is made through the bone from point 105 to point 101. Once the hole (shown in FIG. 13) and cut (shown in FIG. 14) have been performed, the slice of tissue defined by the area ventral to the dotted line in FIG. 14 can be removed. Removal of this slice will relieve pressure associated with the ventral aspect of the SAP pressing on the neural structures in the foramen or lateral recess. The terms "cut" and "hole" can be used interchangeably herein, though in general the term "hole" implies the cut hole inner circumference is similar to the cutting tool circumference (outside diameter), whereas a "cut" implies that the cutting length is longer than the circumference of the cutting tool.

FIG. 15 illustrates a tissue removal technique according to a fourth embodiment of the present invention. Rather than the three-step procedure described above, FIG. 15 describes an alternative procedure for removing tissue pressing on neural structures. FIG. 15 shows an alternative method where, rather than cutting through the SAP as in the first step, the surgeon would sweep a cutting tool back and forth between point 100 to point 101 to thereby creating a cut groove that would continue to get deeper (from medial to lateral) in the SAP until the ventral slice of the SAP being targeted for removal is not substantially attached to the dorsal aspect of the SAP.

FIG. 16 is an axial view of the spine showing the straight (labeled Rt. Path A) and curved trajectory (labeled Rt. Path B) of the cutting tool in the first step of the three-step method described above. The origin of path A and path B in FIG. 16 is the same point shown at point 100 in FIGS. 2, 3, 4, 5, 6, 7, 8, 9 and 10.

Devices for Cutting Tissue:

Selective tissue cutting in the present invention is accomplished by a device capable of selectively cutting or removing hard structures like bone, calcified ligament or disc, while not traumatizing soft structures such as nerve tissue, arteries, veins and muscle. Devices that can achieve this goal include mechanical rotary devices, reciprocating devices (including rotary or linear motions), vibrational devices, ultrasonically-driven devices, and ablation energy forms such as radio frequency or laser.

Mechanical rotary devices are rotated at high frequencies such as ~100 to 100,000 revolutions per minute (RPM). To help selectively cut hard tissue and not soft tissue, in one embodiment, the drill tip has a specific shape, including a tapered, bi-conical shape having portions of the outer surface with roughened elements or cutting elements. The cutting tip of the device can optionally be attached to a drive element that has some flexibility out of the axis of the elongate drive element. This flexible connection between the cutting and distal drive elements allows the cutting element to flex or bounce off soft tissues since the cutting material is itself compliant and the tip of the cutting assembly also has some compliance. In contrast, targeted rigid material such as bone will have a greater tendency to be engaged with the cutting element and be cut since rigid material cannot bounce out of the way as easily. Another variant of a mechanical rotary device for cutting or boring a hole for head-on cutting includes a device with a clutched cutting element that only engages with the drive system when a head-on pressure is applied (i.e., bony structures). Other variants of clutched devices that will limit the cutter to bone and not soft tissues such as neural structures include: a device that stops axial rotation when the required torque is lower than a pre-determined threshold. This feature is opposite of many consumer hardware drills solutions where the drills are clutched to stop rotation of the drill when torque too high. The pre-determined torque setting could be controlled through feedback obtained through a strain gauge or by measuring the input current required to drive the rotational shaft by its respective motor. Side-cutting tools could be made smart by providing feedback on bending moments on the tools through strain gauges or motor current. With the side cutting tools the current or bending moment measured would need to be large enough activate the cutting element which is rotated or reciprocate. Bending moment or axial torque (for rotational device) sensor can be based on a variety of technologies including strain gauge, pressure gauges, motor current draw level or drive motor power or current levels.

Figure 17:
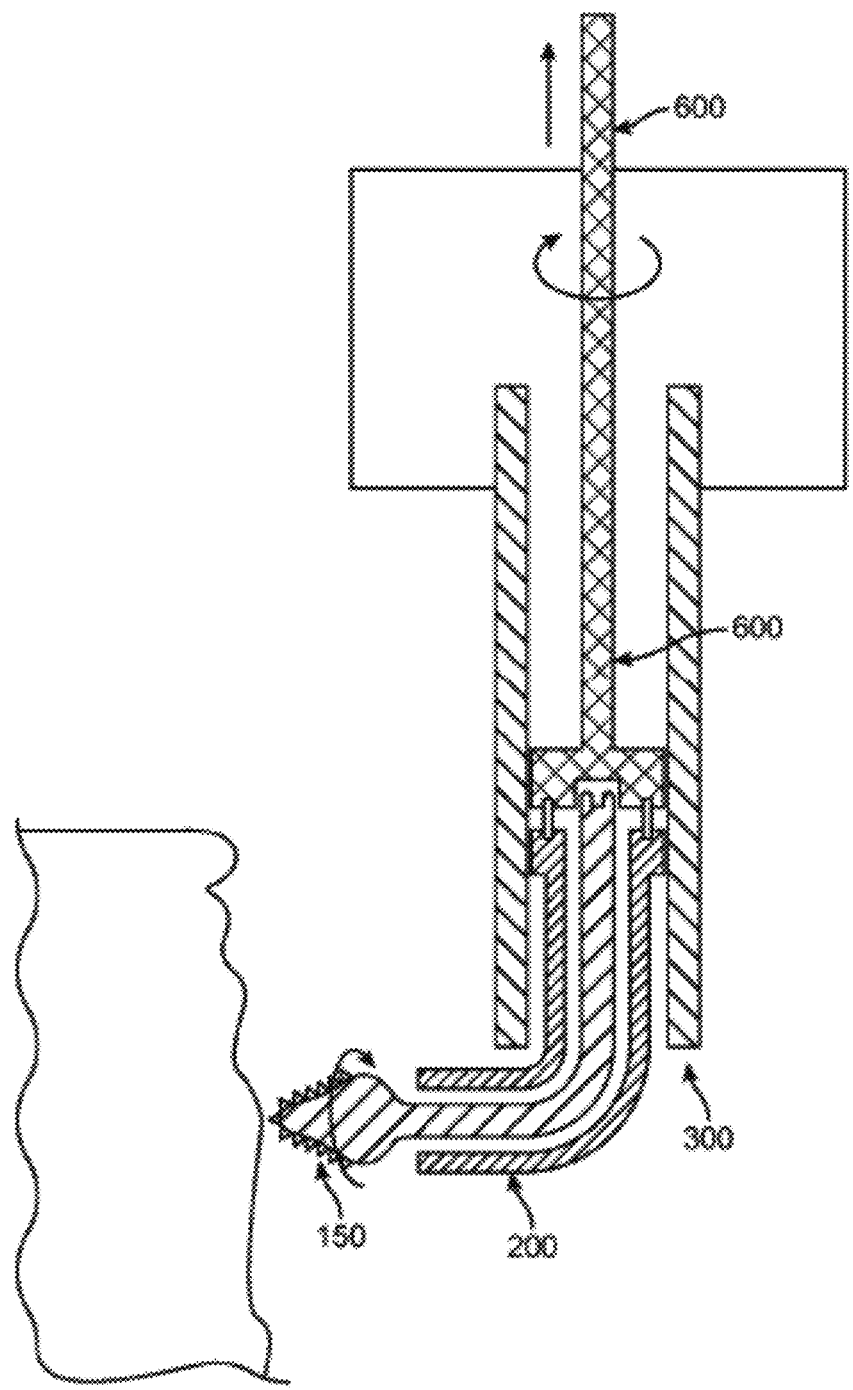
FIG. 17 is a cross-sectional view of a clutched deployable rotary device for head-on cutting.
Figure 18:
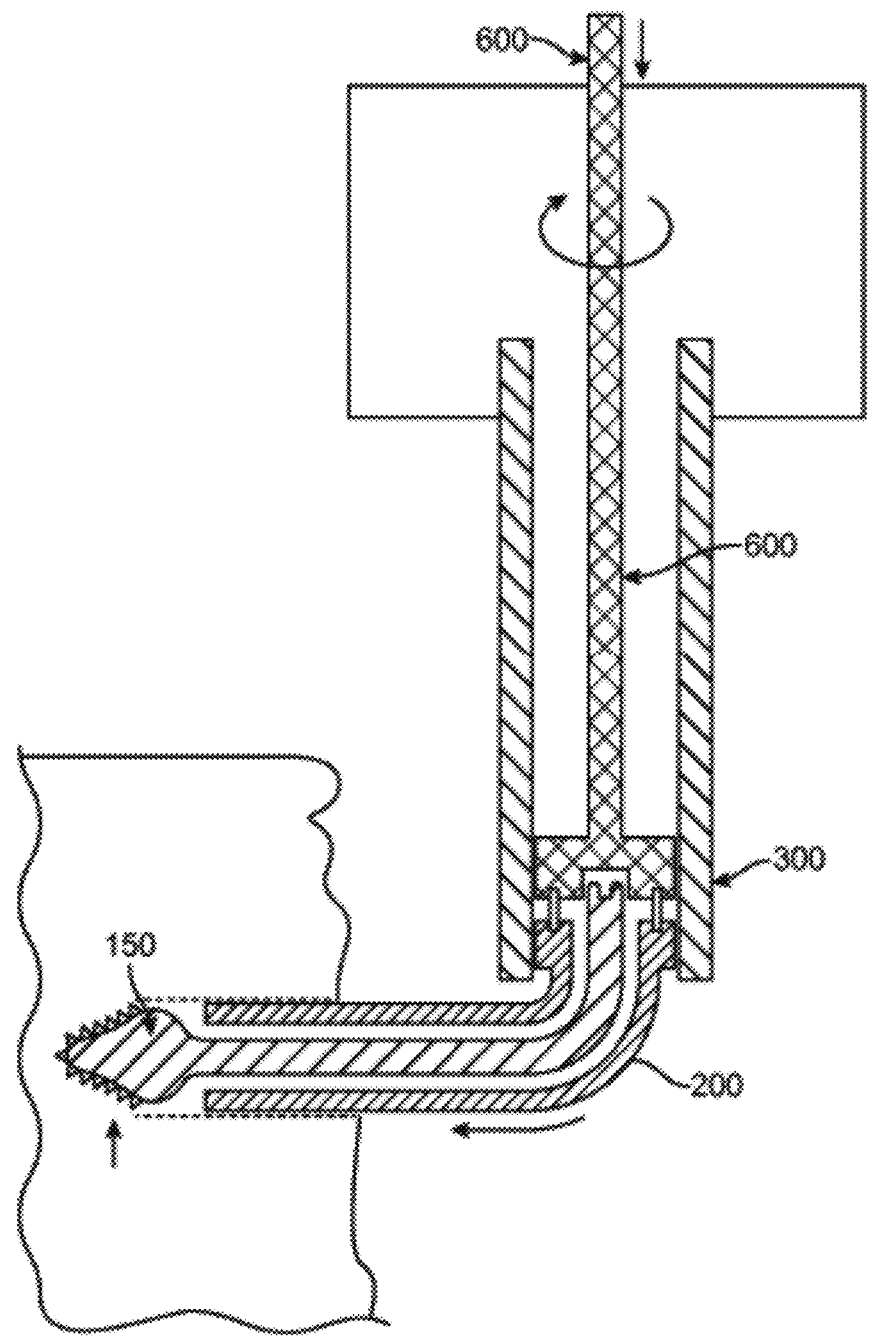
FIG. 18 is a cross-sectional view of the device of FIG. 17 shown in operation.

FIGS. 17 through 18 illustrate one example of a clutched deployable rotary device for head-on cutting. FIG. 17 illustrates the device in a partially-deployed orientation. The device includes an outer guide 300, and a telescoping sleeve 200 that receives a cutting element. A cutting head 150 is carried on the end of the cutting element. When the user deploys the drive shaft 600, which can both be translated and rotated about its long axis by a power system, the telescoping sleeve 200 is passively deployed out of the outer guide 300. The telescoping sleeve 200 has a preset curve that returns to its preset original shape when it is no longer constrained by the outer guide 300. The telescoping drill sleeve 200 will control the trajectory of the cutting head 150 through the targeted tissue. The telescoping sleeve 200 does not rotate as it is not rotationally coupled to the drive shaft 600. Irrigation can be provided inside the telescoping sleeve 200 to ensure that the device does not overheat. The device in FIG. 17 can be powered by a rotational drive source and optionally includes a clutch mechanism (not shown). FIG. 18 illustrates the device in a deployed orientation, where the telescoping sleeve 200 has been further deployed and the cutting head 150 has cut a track in the targeted tissue. In any of the cutting devices in this application the cutting tool may be cooled with a variety of methods including room temperature or chilled saline which may be passively dripped or actively pressurized through or around the cutting device assembly (not shown). Cooling the cutting tool may help prevent the cutting device or adjacent tissues from getting overheated. Alternatively a separate device could be used to deliver irrigation near the cutting device to prevent overheating and/or an integrated or separate aspirational tool may be used to remove the irrigation that is introduced near the targeted tissue.

Figure 19:
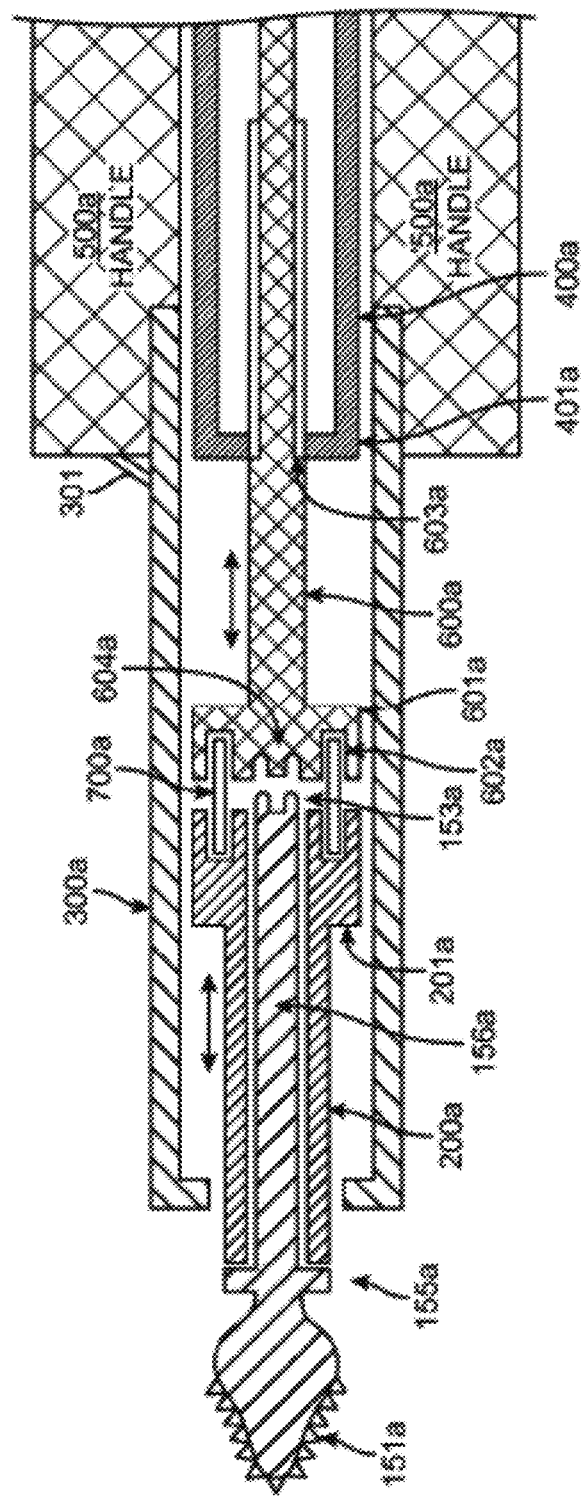
FIG. 19 is a cross-sectional view of a clutched and telescoping cutting device according to another embodiment of the present invention.

FIG. 19 is a cross-sectional view of a clutched and telescoping cutting device according to another embodiment of the present invention. The cutting device in FIGS. 19 and 20 has a drill element which includes a flexible drill drive mechanism 156*a* which allows the distal end of the device in FIG. 19 to adapt to curved trajectories yet still be efficient at transmitting torque. Examples of constructions for the flexible drill drive mechanism 156*a* can include dual-winded coil constructions optionally wound about a stiffening core. An optional stop lip or shoulder 155*a* can be provided along the drill drive mechanism 156*a* adjacent a cutting tip 151*a*. The drill drive mechanism 156*a* is housed for reciprocal movement inside a guide element 200*a* which has a proximal end 201*a* with a recess in which a portion of a spring element 700*a* is positioned. The remainder of this spring element 700*a* is retained inside a distal recess or hole 602*a* provided at the distal end 601*a* of a push rod 600*a*. The push rod 600*a* can be pushed or pulled by the user to deploy the device as desired. In other words, the push rod 600*a* can be translated and rotated along its longitudinal axis. The spring element 700*a* is compressed by axial loads exerted from the cutting tip 151*a* on hard tissue. During this compressive load, the cams 153*a* on the drill element 150*a* engage corresponding female recesses 604*a* of the push rod 600*a*. This engagement allows the rotational force of the push rod 600*a* to drive the drill element 150*a*. Once the compressive loads are abated (e.g., when the cutting tip 151*a* is passed through bone to soft tissue), the spring element 700*a* will bias or push the push rod 600*a* away from the guide element 200*a*, thereby preventing the drill element 150*a* from being actively rotated.

An outer cannula 300*a* houses the guide element 200*a* and the push rod 600*a*, and is rigidly attached to a handle 500*a*. Splines 603*a* are provided on the outer surface of the push rod 600*a* to allow rotational force to be transmitted from a drive collar 400*a*. The drive collar 400*a* extends inside the handle 500*a* and a portion of the outer cannula 300*a*, but does not translate with respect to the handle 500*a*. The drive collar 400*a* is rotated through torque transmission by an on-board motor or external rotational drive source (not shown). The drive collar 400*a* has feet 401*a* which include grooves that engage the splines 603*a* on the push rod 600*a*.

Thus, FIG. 19 illustrates the interface between the telescoping guide element 200*a* and the push rod 600*a*. The push rod 600*a* is actively rotated and has recesses located in its distal end 601*a*. The spring element 700*a* can be retained (without being affixed) in the space defined by the recesses 201*a* and 601*a*, or can be attached to the recesses 201*a* and/or 601*a*. This spring element 700*a* is not intended to carry torque loads to rotate the drill element. To allow for retraction of the guide element 200*a* when the push rod 600*a* is retracted, a tether (not shown) can be provided between the guide element 200*a* and the push rod 600*a*.

Figure 20:
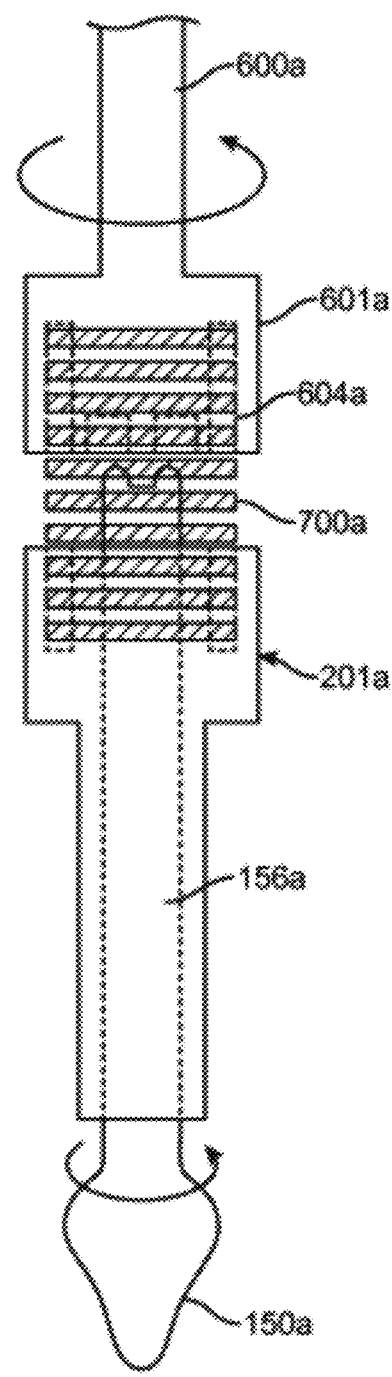
FIG. 20 illustrates the operation of the spring element of the device in FIG. 19.

FIG. 20 shows a cross sectional view of the spring element 700*a* described in FIG. 19. Spring element 700*a* will only allow the push rod 600*a* to engage with the drill drive mechanism 156*a* when pressure is applied to the drill bit.

To achieve the second and third steps described in FIGS. 7-11 above, it may be desirable to use a side-cutting mechanical device to achieve the cut. Such side-cutting devices could include reciprocating linear or rotating elements, or simply rotating elements. It may be desirable to have the cutting elements clutched where they are only active/moving when the device is engaged with the targeted tissue, and more specifically hard tissue such as bone. Having a clutched mechanism would provide additional control so that the surgeon does not inadvertently cut soft tissue such as nerve or blood vessels.

Figure 21:
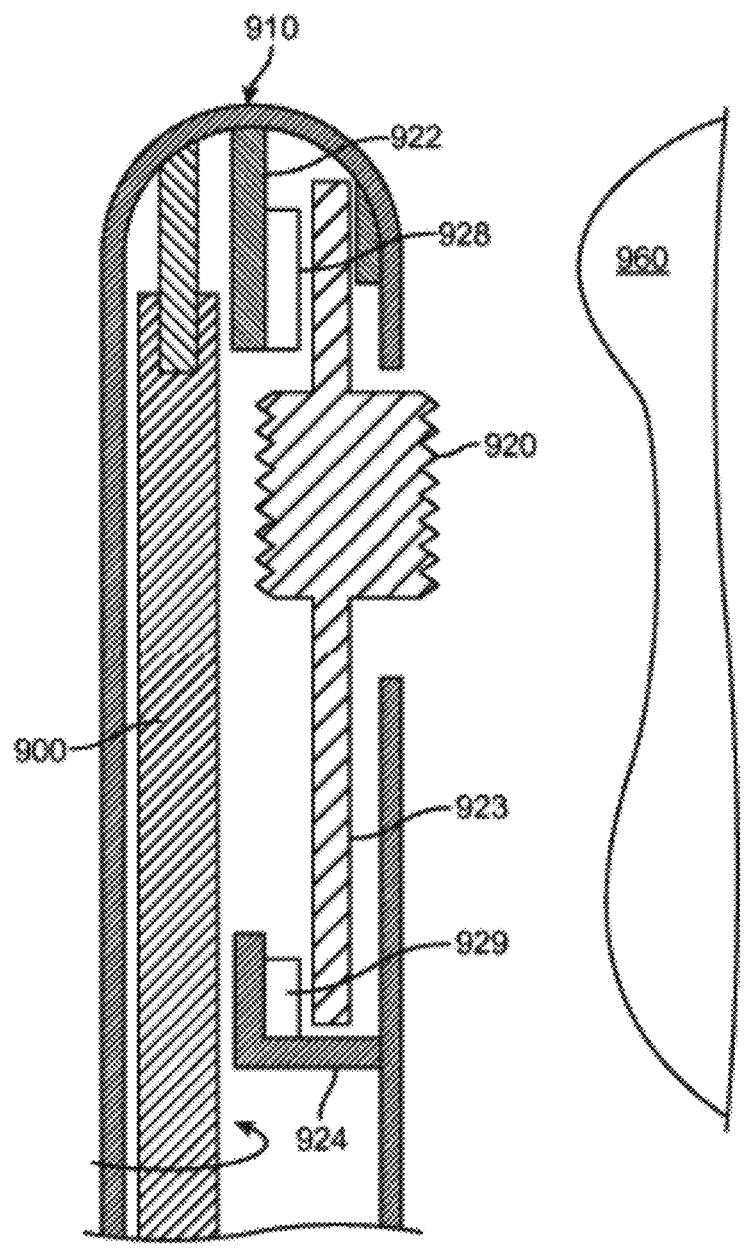
FIG. 21 is a cross-sectional view of a clutched side-cutting rotary device according to the present invention.
Figure 22A:
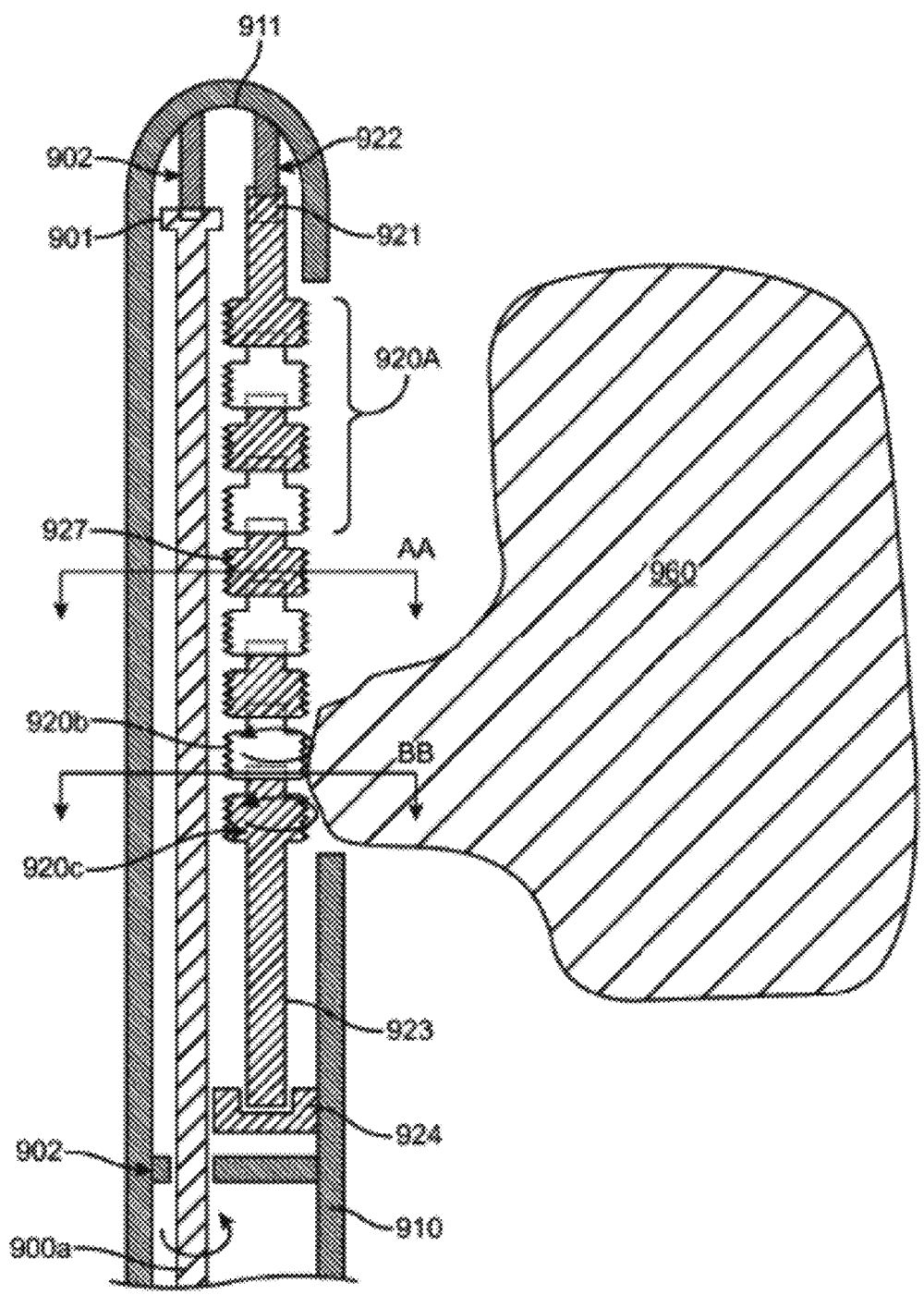
FIG. 22A is a cross-sectional view of a clutched side-cutting device with multiple cutting elements according to the present invention.
Figure 22B:
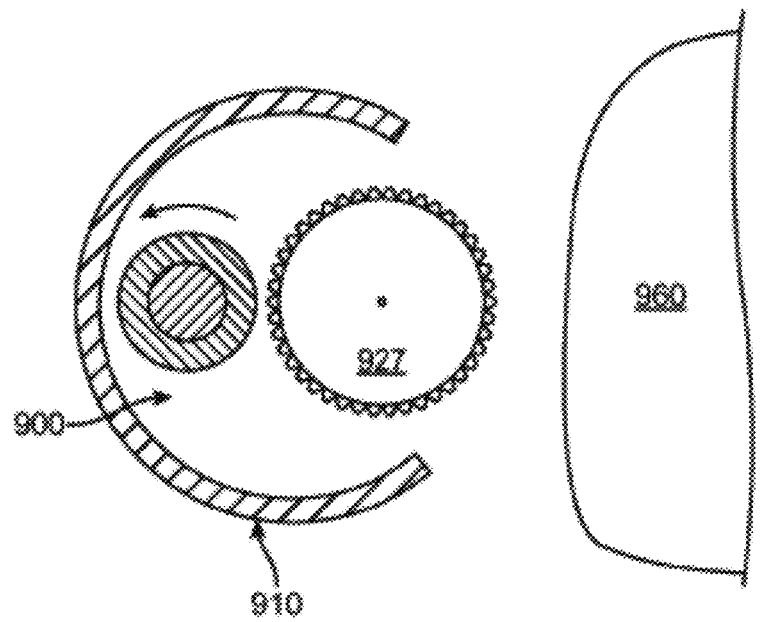
FIGS. 22B and 22C are cross-sectional views taken along the lines AA and BB, respectively, in FIG. 22A.
Figure 22C:
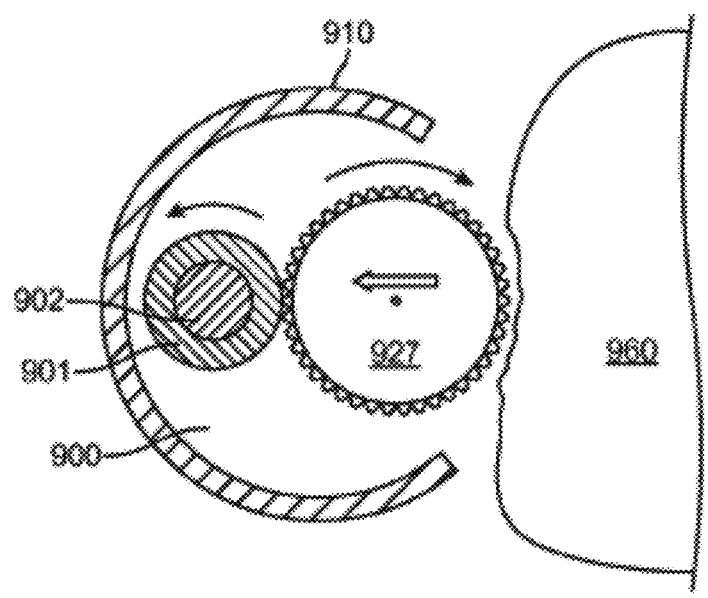

One example of a clutched side-cutting rotary device is shown in FIG. 21. In FIG. 21, a drive shaft 900 and a passively activated cutting element 920 are housed inside a cannula 910. The cutting element 920 can passively rotate or translate up to a few millimeters from the inside edge of the cannula 910, and is positioned adjacent a window or opening in the cannula. An alternative to the single side-cutting element 920 shown in FIG. 21 is to provide a series of side-cutting elements 920A as shown in FIG. 22A. When the cutting element 920 is proximate with targeted tissue 960 and a pressure is applied, the cutting element 920 can translate towards the actively rotating drive shaft 900. When physical contact is made between the cutting element 920 and the drive shaft 900, the cutting element 920 will also rotate to cut the targeted tissue. When no force is applied to the cutting element 920, it springs back to its original position where it does not contact the shaft 900. FIG. 22B shows the cutting element 920 positioned in its original position from an axial view. FIG. 22C shows the cutting element 920 being actively engaged with the drive shaft 900 as pressure is applied with the cutting element 920 contacting the targeted tissue 960.

One way to ensure that the cutting element 920 returns to its original position when it is not loaded is to use spring elements 928 and 929 that are positioned in receptacles 922 and 924, respectively, that are located between the distal and proximal end of the cutting element 920. When an orthogonal load is applied to the long axis of the cutting element 920, these springs 928, 929 compress and allow contact with the drive shaft 900. The springs 928, 929 can be tuned so that the cutting element 920 disengages from the drive shaft 900 when the cutting element 920 cuts through hard or boney tissue to be in contact or proximate with soft tissue such as a nerve. Other alternative mechanisms could make sure that the cutting element 920 return to its original position. For example, the cutting element 920 can be configured such that its proximal and distal ends can flex or bend when force is applied, but spring back to its desired straight orientation when there is no load. Alternatively, the drive shaft 900 can be provided with a compressible and elastic outer shell which can also achieve the same objective. Specifically, the compressible and elastic shell would spin independently of the drive shaft 900. When compression loads are applied between the cutting element 920 and the shaft 900, the compressible elastic shell would act like a clutch and aid in transmitting torque between the two structures. In addition, while FIG. 21 shows that the serrated portion of the cutting element 920 is configured to make direct contact with the drive shaft 900 to rotate, it may be desirable to have a non-serrated or sharp area of the cutting element 920 to make contact with the drive shaft 910 (not shown). Another alternative includes a shaft of the cutting element 920 that may have gears on its outer surface that are indexed with the drive shaft 900 to make a more efficient transmission of rotation.

Ports (not shown) may also be provided in the cannula 910 to allow for both delivery of irrigation (such as saline) to keep the system cool, and aspiration to allow for removal of debris created from the cutting process. If the side cutting device shown in FIG. 21 were to be used inside a hole as described in the first step above to cut a slot through bone (see FIGS. 7 and 8), it may be desirable to sweep the cutting element 920 back in forth in the hole while applying side loads to achieve the cut line from point 101 to point 102 in FIGS. 7 and 8.

An alternative to the single side-cutting element 920 shown in FIG. 21 is to provide a series of side-cutting elements 920A, as shown in FIG. 22A. This type of design would allow selective cutting along any one of the cutting elements 920A when pressure is applied to each specific cutting element 920A. Such a design would avoid the need to sweep the side-cutting device back and forth inside of a hole to achieve side cutting. FIG. 22A shows a series of cutting elements 920A having portions thereof nestled inside an adjacent cutting element 920A. Enough radial slop or distance is provided between the nestled cutting elements 920A to allow each cutting element 920A to independently slide over to engage with the drive shaft 900 without pulling an adjacent cutting element 920A along with it. Cutting elements 920*b* and 920*c* are engaged with the drive shaft 900*a* since the cutting element(s) are making contact with the targeted tissue 960. The resulting cross-sectional of this schematic is depicted in FIG. 22C. In this situation, the other cutting elements are not actively under pressure and therefore are in their original positions (i.e., spaced-apart from the drive shaft).

FIG. 22B is a cross sectional view of a cutting element 927 of FIG. 22A in its original non-deployed position. To help the cutting elements 927 to return to their original positions when not loaded, the drive shaft 900 shown in FIG. 22C has a compliant and elastic outer shell 901 with a rigid inner core 902 to enable efficient rotation of the drive shaft 900.

Another technology that can be used to achieve selective cutting of hard versus soft tissues is vibrational energy or ultrasound energy that may cut through targeted tissue as described in the first step above. Such a first step may be achieved by deploying a vibrational device that has a distal end or tip portion at an angle of 10 to 200 degrees off the longitudinal axis to directly approach target tissue. In one embodiment, such a vibrational device may be provided in the form of a rigid cannula with any desirable angulations. In another embodiment, the vibrational device may be a flexible or steerable catheter suitable for re-direction around a specific curve trajectory.

Figure 23:
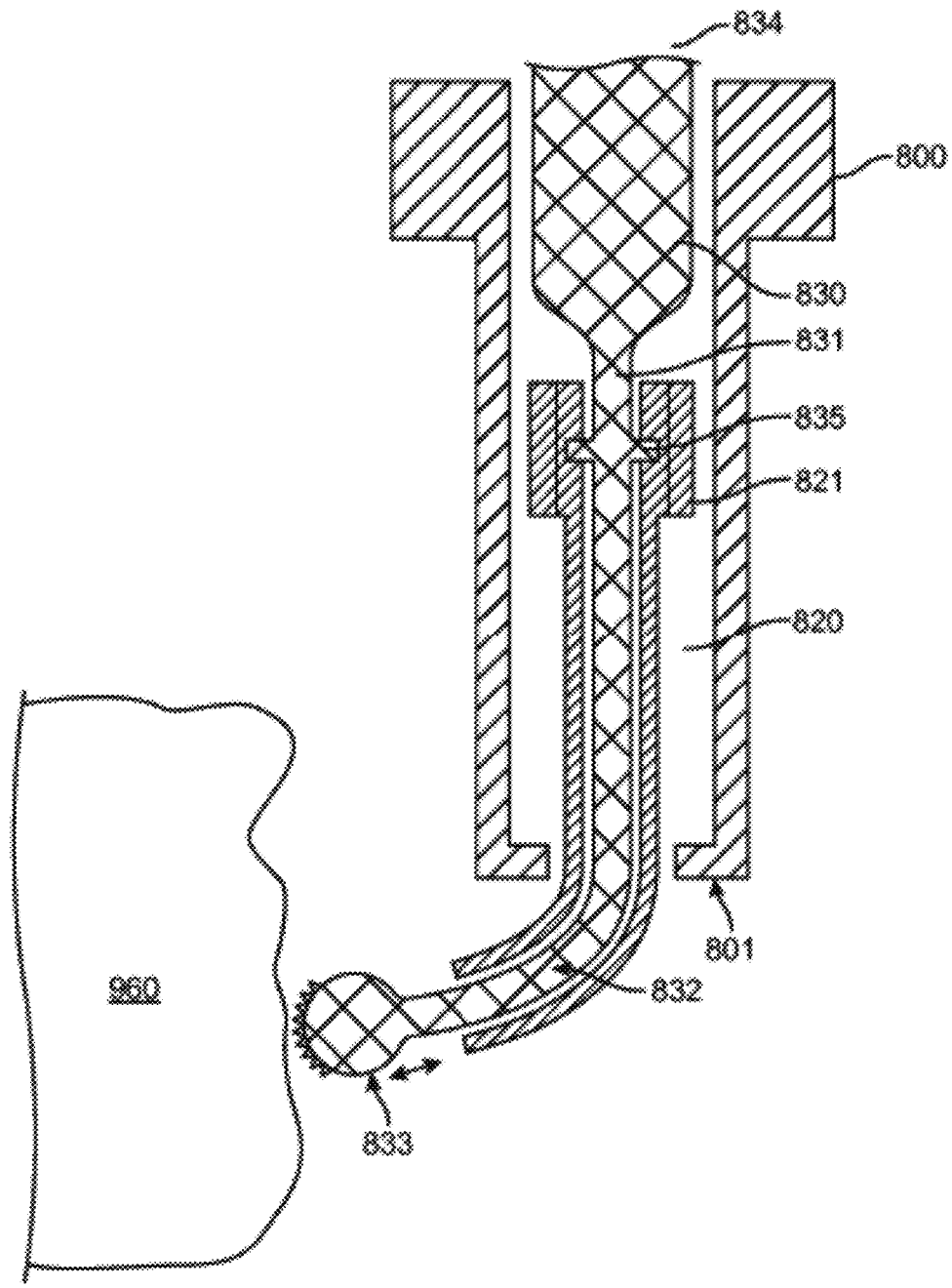
FIG. 23 is a cross-sectional view of an ultrasonic cutter according to the present invention.
Figure 24:
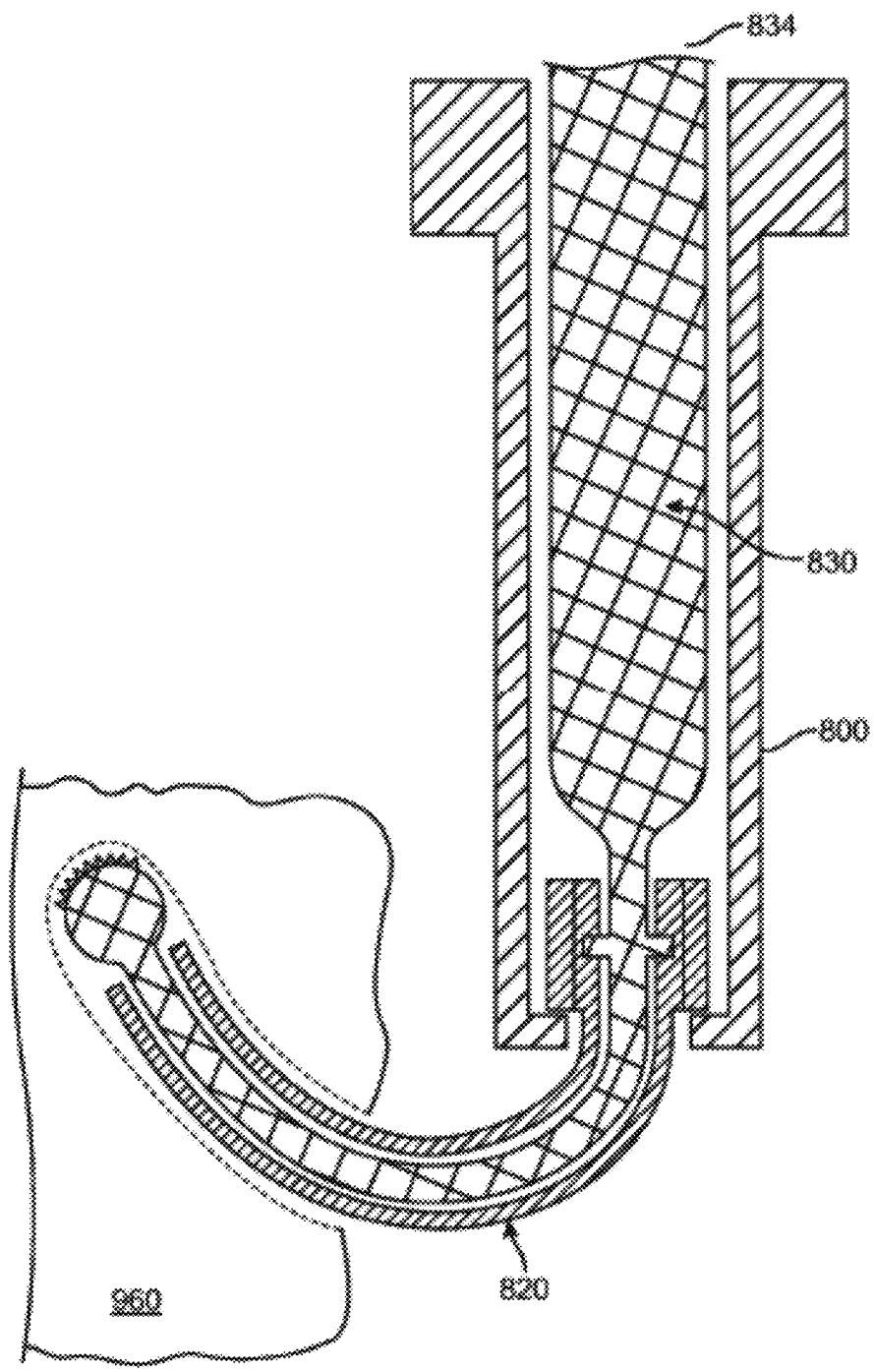
FIG. 24 is a cross-sectional view of the device of FIG. 23 shown in operation.

FIGS. 23 and 24 illustrate an example of a vibrational device having a proximal portion 830, a mid-portion 831, a distal portion 832 and a distal tip 833, with the distal portion 832 and the distal tip 833 capable of extending through a specific trajectory and into the targeted tissue 960. The vibrational device can be housed inside an outer rigid guide 800. To control the trajectory of the distal portion 832 and the distal tip 833, a shape memory guide 820 having a distal portion and proximal portion 821 is provided inside the rigid guide 800 to house the distal portion 832 of the vibrational device. Such a shape memory guide 820 can be made from a variety of constructions, including materials such as Nitinol, Peek, etc. The mid-portion 831 has a step 835 that is attached or affixed to the proximal portion 821 of the shape memory guide 820, and both are located inside the rigid guide 800. When the shape memory guide 820 and distal portion 832 of the vibrational device are deployed out the distal end of the outer guide 800, the shape memory guide 820 is no longer unconstrained, and is able to assume its curved trajectory. The curved shape memory guide 820 dictates the trajectory of the distal tip 833 against the target tissue 960. FIG. 23 shows the distal portion 832 and the shape memory guide 820 partially deployed outside of the rigid guide 800, and positioned against the target tissue 960 with initial angulations, while FIG. 24 shows the same apparatus fully deployed outside the rigid guide 800 with a full predetermined shape/angulations.

Vibrational energy or ultrasound energy generates heat when propagated from the energy source, which can be a piezoelectric transducer (not shown) located on the proximal portion 830 of the vibrational device. To avoid the impact of such heat on the treated tissue, irrigation or cooling is provided around the vibrational device. Such irrigation or cooling medium can be a sterile solution of sodium chloride (0.9% NaCl) which helps to wash out particles generated by the vibrational device during or after cutting. A sterile solution may further be aspirated and removed outside of the treatment location. Vibrational or ultrasound frequencies used to drive such tools may be within the range of 1 Hz-1 MHz, and preferably 20-100 kHz. The length of such vibrational devices may vary between 1-100 cm. Vibrational devices may operate in continuous mode, pulse mode, or a combination of both. Ultrasound energy may be modulated by frequency, or electrical voltage delivered to the transducer.

Figure 25:
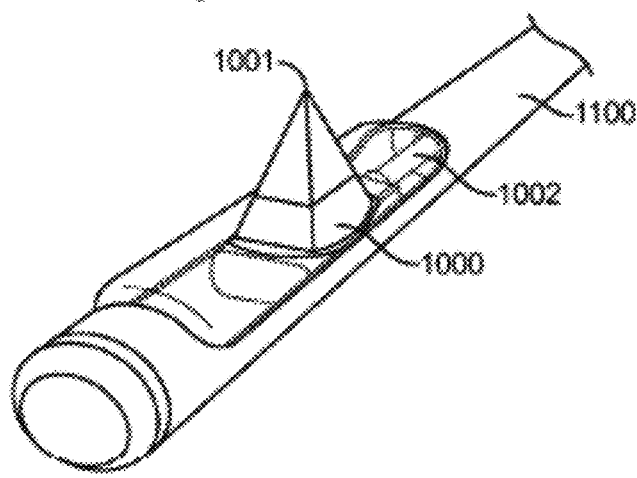
FIGS. 25 and 26 illustrate two different types of side-cutting ultrasonic cutters.
Figure 26:
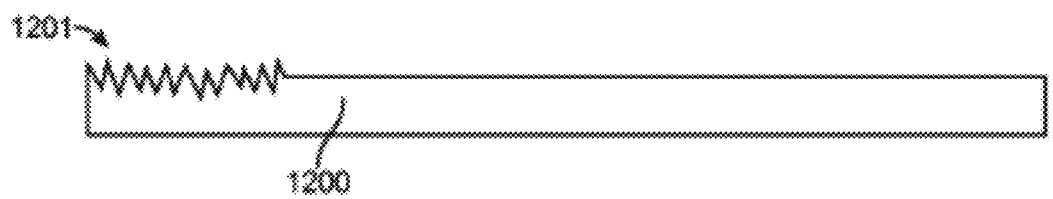

In FIGS. 25 and 26, ultrasound cutting elements are shown that can be used to achieve the second and third steps (side cutting) described above, and can be deployed through a guide device to help achieve the best results. In FIG. 25 element 1000 is vibrated with respect to the cannulated housing 1100 at ultrasonic frequencies. Cutting element 1000 is shown to have a pointed cutting tip 1001 to concentrate the cutting action at that the point. The cutting tip 1001 is attached to a transmission shaft 1002 which is driven by the ultrasonic power source. Coolant can be delivered through the cannulated housing 1100 to protect the device or contacted tissue from excessive temperatures. In FIG. 26, the cutting element 1200 has serrations 1201 on its distal end and would be attached to an ultrasonic power source on the proximal end. These serrations 1201, when put in contact with hard tissue with some applied force, will cut in the direction of the applied load. Cutting element 1200 could be stiff, flexible, straight and/or curved. If the cutting element 1200 is flexible, it may be desirable to house the cutting element in a pre-shaped guide as shown in FIG. 24 (e.g., such as in a guide 820) to provide some rigid support to allow the surgeon to apply the desired contact forces to the targeted tissue.

Alternative Methods to Cutting the Ventral Aspect of the SAP/IAP Joint Using a "Far Lateral Approach Method"

An alternative to the method shown in FIG. 3 where the entry site for the cutting hole 100 is created from a paramidline approach, this method involves creating a hole in the first step from a lateral approach by starting lateral of the SAP. Once the hole is initiated the hole/slot is continued and directed medialymedially. This approach is often referred to by surgeons as a "far lateral foraminal decompression approach". When drilling/cutting the hole from the lateral approach, endoscopy, microscope, loops, triggered EMG and/or fluoroscopy can be used to aid in locating the lateral aspect of the SAP where the cutting would begin. When drilling the hole when the cutting tool cuts though the medial aspect of the SAP/IAP, ligament will usually be present before hitting the dura. Therefore, the ligament flavum can act as a barrier to help prevent inadvertently tearing the dura, nerve root or cauda equina. Also, when used in combination with 'smart' cutting tools that differentiate between hard tissues (bone) versus soft (nerve/dura), the ligament will assist in ensuring that the cutting tools do not cut through and into the dura/nerve. Examples of "smart" cutting tools include but are not limited to devices having a local visualization implemented into their structure.

Once the first step has been completed using a "Far Lateral Approach Method, the second and third steps can be carried out as previously described, but from the lateral side of the SAP. From this lateral technique, the surgeon can alternatively sweep a cutting tool back and forth between the caudal and cephalad portions of the SAP to thereby create a cut-groove that would continue to get deeper (from medial to lateral) in the SAP until the ventral slice of the SAP being targeted for removal is not substantially attached to the dorsal aspect of the SAP. Using a pituitary or other tool, the cut portion of the SAP can then be extracted.

Imaging Embodiments

In some embodiments, Optical Coherence Tomography (OCT) may be employed in lieu of, or in combination with, endoscopy. OCT is an optical signal acquisition and processing method, typically employing near-infrared light. The use of relatively long wavelength light allows it to penetrate into the scattering medium. It captures three-dimensional images from within optical scattering media, such as biological tissue or blood clots. Examples of such systems include, but are not limited to, devices from Coherent Diagnostic Technology (CDT), LLC, based in Westford, Mass.

In other embodiments, an ultrasound device can work in conjunction with an endoscope system which includes a working channel for therapeutic devices to be introduced. The working channel of the endoscope may accommodate the ultrasound device and can serve as an outlet to remove blood clots. Examples of such devices include, but are not limited to, endoscopes from Pentax Medical Company, New Jersey; Olympus America, Center Valley, Pa.; Richard Wolf GmbH, Knittlingen, Germany.

In yet another embodiment, an imaging camera may be provided on the distal end of an ultrasound device. Such electronic imaging camera may have a light emitting source provided by light emitting diodes (LED) or by light delivered via fiber optics from an external source. The principles of operation are identical to endoscopes, but in this case the camera is incorporated in a single device together with the ultrasound device. Examples of such suitable cameras include, but are not limited to, devices from MediGus, Ltd, Omer, Israel; OmniVision, Santa Clara, Calif.; Clear Image Technology, Elyria, Ohio; Awayba, Nurnberg, Germany.

Endoscopy such as a fiberscope, rigid reusable scope or CMOS based disposable scope can also be used to aid in any of these methods described above. The endoscope can be mounted or affixed to the cutting tools described in FIGS. 17, 21, 22, 23, 25 and 26. Alternatively the endoscope can be independent or attached to a suction or irrigation device.

Alternatively, a hand held mirror tool could be used to allow the surgeon to look around the corner in the surgical exposure. The mirror could be flat, concave or convex and would be sized appropriate to fit into the surgical exposure (2-15 mm in diameter). The mirror could have an integrated light source or it could receive light from other equipment such as a microscope. Also, the mirror could have an irrigation port near the mirror surface to help clear away any debris which could affect visualization. Lastly, the mirror element could be integrated onto a cutting tool or a suction device to reduce the number of tools the surgeon needed to manipulate at one time.

"Smart" Cutting Devices

Some other embodiments of the present invention include "smart" devices capable of differentiating between soft tissue and healthy tissue and hard bony structure. Healthy tissue (including nerves) is highly elastic and will not get ablated or injured unless a very high mechanical vibrational energy is delivered to the specific area that will cause a local damage or obliteration. Such "smart" devices can include ultrasound devices that utilize vibrational energy that is propagated along a side cutting member, such as shown in FIGS. 25 and 26. The ultrasound devices delivering vibrational energy to the bony structure utilize at least three principal modes: longitudinal waves, shear (transverse) waves and surface (radial or elliptic) waves, among other ultrasound waves that are not contributing to the cutting process. In longitudinal waves, the oscillation occurs in the longitudinal direction or the direction of wave propagation. In shear waves, oscillation occurs transverse to the direction of propagation. Such transverse waves are relatively weak compared to longitudinal waves. Surface waves are mechanical waves that propagate along the interface between differing media. Surface waves travel the surface of a solid material or liquid penetrating to a depth of one wavelength. Surface waves combine both a longitudinal and transverse motion to create an elliptic orbit motion. The major axis of the ellipse is perpendicular to the direction of the propagation of the waves. While the time of ultrasound energy exposure depends on bone structure and the size of the particular disease, the exposure time within the treatment area can be anywhere between 1 second to 60 minutes, and the ultrasound power delivered should not exceed 100 Watts, to avoid damage to healthy tissue.

Additional Device Variations

In general, any of the apparatuses described herein may include any of the features or elements (including the cutting, e.g., drilling, ultrasound, etc., elements) of any other embodiment.

Figure 27A:
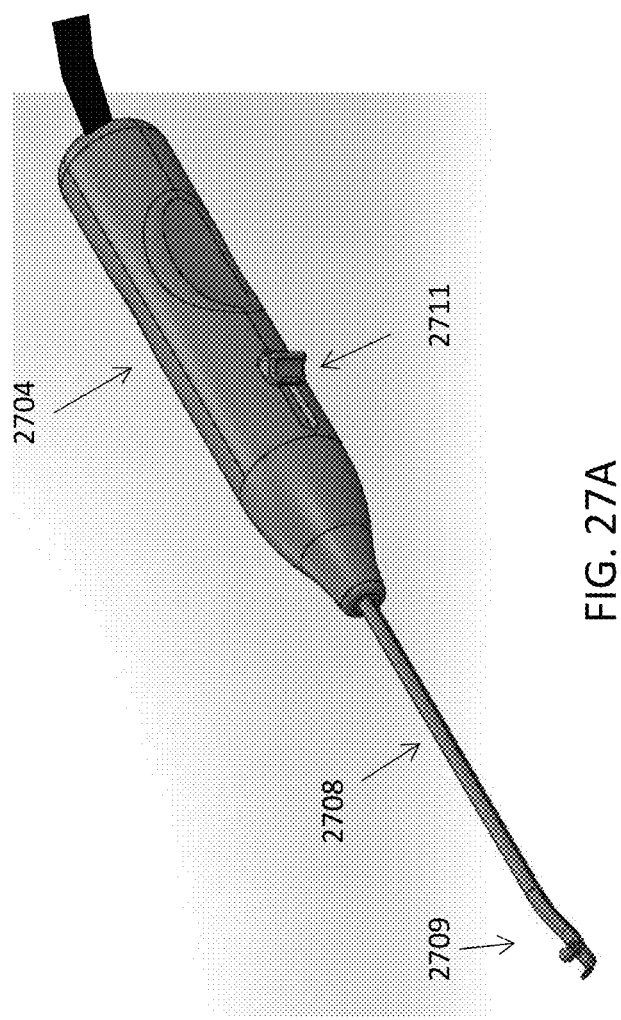
FIGS. 27A and 27B illustrate side perspective and side views, respectively, of another variation of a deployable rotary tool.
Figure 27B:
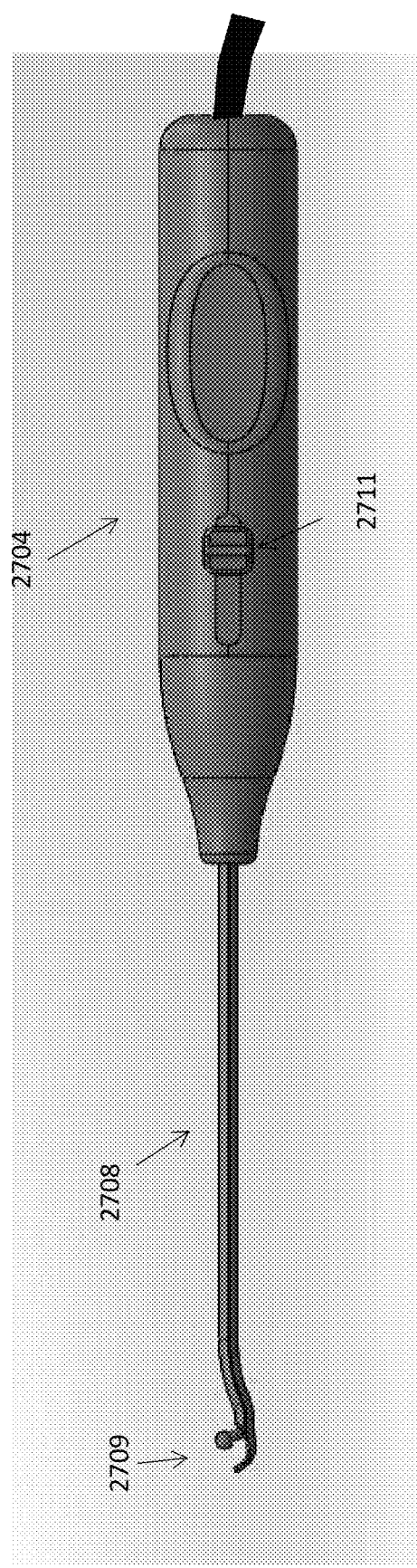

For example, FIGS. 27A-27B illustrates another example of an apparatus that may be used as described herein. In this example, the apparatus includes a proximal handle 2704. In any of these variations, the handle may include an integrated battery and drive mechanism for rotary or reciprocating motion. The handle may house these elements, including mechanical and/or electrical elements, such as gears, motors, circuitry, etc. The device shown in FIGS. 27A-27B also includes an optional connector for an external drive mechanism and/or power supply. Other connectors, as mentioned above, including suction/perfusion, optical fibers, etc., may also be included and integrated into the handle or elongate intermediate region 2708 connecting the handle to the distal end 2709. The handle may also include one or more controls (switches, dials, etc.) and/or indicators. For example, in FIGS. 27A-B, the apparatus includes a slider switch to deploy drill bit.

In general, the intermediate region may be a rigid and/or bent/bendable member, such as a cannula. The intermediate region may be referred to herein for convenience as a cannula or guide cannula, and may be shaped to aid in position the distal end of the apparatus, e.g., between adjacent bone regions, such as medial to the SAP, and may help support deployment of the distal end of the apparatus, which may include a reciprocating (e.g., rotating) member and/or a drive shaft to enable reciprocation of the cutting element and/or imaging element. The intermediate region may be cylindrical over all or a portion of its length. In some variations all or a portion is flattened (e.g., oval, rectangular, etc.). For example, the distal end region may be flattened to allow access into narrower body regions. The intermediate region (cannula) maybe formed of a material such as stainless steel, a shape memory alloy (e.g., nickel titanium, such as Nitinol), polymers (particularly stiff polymers), or combinations of materials, including materials having different stiffnesses. The distal end region (near the distal end/tip of the apparatus) of the intermediate region may be curved or bent.

Figure 28B:
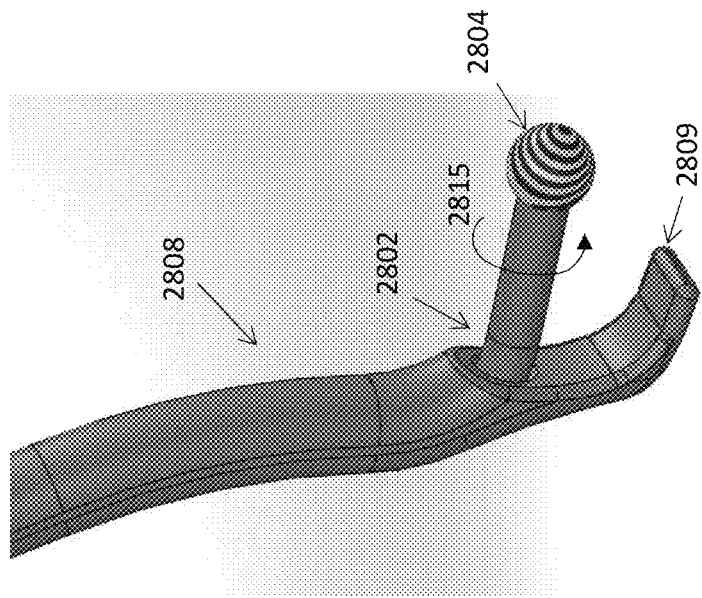
FIGS. 28A and 28B illustrate another variation of a deployable rotary device having a telescoping end on drill bit in a retracted, as shown in FIG. 28A, and extended, as shown in FIG. 28B, configuration.
Figure 28A:
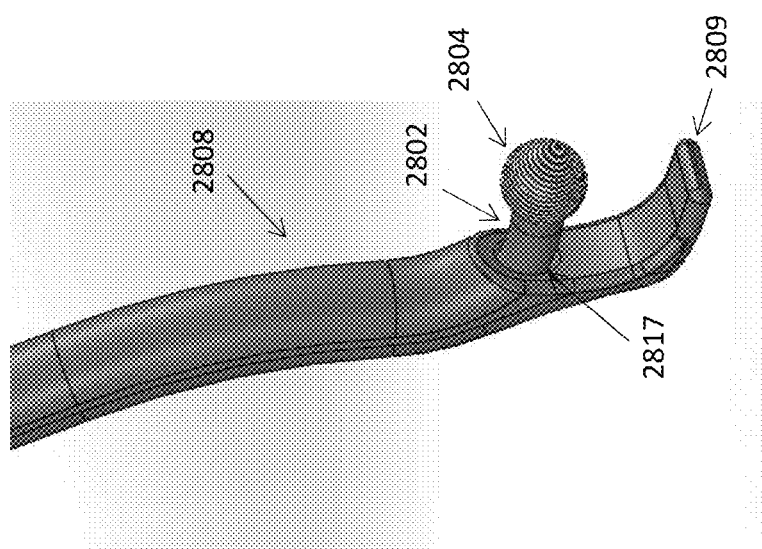

For example, FIGS. 28A and 28B illustrate another variation of a tool for cutting the spinal bone as described herein. In this variation the tool is a drill device that is configured to cut bone in an articular process (e.g., SAP). In this example, FIG. 28A shows the distal end of the cannula (intermediate region 2808). The distal end includes a rotating cutter, shown as a drill bit 2804 having a spherical profile at the end of a flexible, pre-shaped drive shaft 2802. The drive shaft may be bent as it exits the cannula. The device includes an index (or guide) lip region 2809 at the distal end, distal to the drill bit. The index region may be formed of the same material as the cannula forming the intermediate region, and from which the drill bit and/or drive shaft extend, or it may be a separate material. The spacing and/or orientation of the index lip may be set based on the target of cutting. For example, the index lip may be separated by a predetermine distance between about 1 and 100 mm (e.g., between a lower value of any one of about 0.5 mm, 1 mm, 2 mm, 3 mm, 4 mm, 5 mm, 6 mm, 7 mm, 10 mm, 15 mm, 20 mm, 30 mm, 40 mm, etc.; and an upper value of any one of about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 20 mm, 25 mm, 30 mm, 40 mm, 50 mm, 60 mm, 70 mm, 80 mm, 90 mm, 100 mm, etc., where the lower value is less than the upper value of any of these ranges). In some variations the spacing between the lip region and the cutting element (drill bit 2804 in FIGS. 28A-28B) may be adjustable. For example, the spacing between the lip region and the midline of the drill bit may be adjustable from the proximal handle by rotating a control, which may be locked in position (not shown). The spacing between the lip region and the midline of the drill bit may be adjusted before the drill is actuated, and locked in position, and/or can be modified when the drill is actuated allowing a user to drill away or towards the lip region in a continuous fashion.

The lip region at the distal end may be configured to more easily slide laterally along the bone being cut. For example, the lip region may include a polished/smooth surface, which may be coated (e.g., with a slippery, non-stick material, such as Teflon, etc.) and/or the lip region may include a rotary element, such as a roller, wheel, etc., for allowing sliding or rolling movement along a bone to be cut. In general, the lip region may be optional. The lip region may be flatted, e.g., particularly as compared to the cannula, and may have a rounded, atraumatic end. Further, the long axis of the lip region (e.g., the axis that extends at an angle from the distal end of the device, and/or relatively to the long axis of the intermediate region) may be fixed or adjustable. In some variations the long axis of the lip region extends from the distal end of the device at an angle that is approximately parallel to the drill bit. Alternatively, the lip may be configured to allow a user to mold or bend the lip region. For example the lip region may be formed of a material that allows a user to mold or bend the lip to a preferred orientation, angle, and/or shape before the lip region is inserted into the surgical site.

In any of the variations described herein, the cutting member (drill bit 2804 in FIGS. 28A and 28B) may be extended from the device by an extending drive shaft, as shown in FIG. 28B. The drive shaft may rotate 2814. In some variations the drive shaft is housed within (and extendable from) the intermediate region (cannula 2808) and may bend as it exits the distal opening (cutter opening). The drive shaft 2802 may rotate 2815 even after/as it is bent. In some variation a sleeve (not shown) may cover the drive shaft, and may be configured to provide a low-friction surface against which the drive shaft may contact even as it bends to exit the distal end of the device. The cutter 2804 (drill bit) may be larger than the distal end opening 2817, preventing it from retracting into the cannula, or it may be smaller than at least the distal most portion of the cannula and the distal end opening 2817, so that the cutting element (drill bit) may be housed/retracted into the cannula either partially or in some variations, completely.

In general, the drive shaft is flexible and may optionally be pre-shaped to assume a pre-determined curvature once deployed outside of the guide cannula. The drive shaft may be formed of any appropriate material. For example, the drive shaft may be formed of one or more of: a co-axial wound coil, a round wire, a flat wire, a stainless steel metal, a shape memory material (e.g., nickel titanium, such as NiTi), a polymer wire, a hypotube (e.g., shape memory alloy hypotube), a composite or combination of any of these.

As mentioned above, in any of these apparatuses, the apparatus may apply irrigation. For example, the apparatus may apply irrigation through and/or around the drive shaft (e.g., between the cannula and the drive shaft).

The cutting element may be a drill bit 2804, as illustrated in FIGS. 28A-28B. A drilling element (drill bit) may be attached and/or integral to the drive shaft, and it may be capable of cutting through bone and/or ligamentous tissue. For example, a drill bit may be formed of a hardened steel and/or may have diamond coatings. The shape (e.g., 3D or sectional shape) may be oval, oblong, cylindrical, round, football-shaped, or any other shape. The surface may include channels, e.g., flutes, etc. or may have other blade patterns to aid in cutting and removing tissue. The drill bit may be any appropriate size. For example, the drill bit may be sized between about 1 to about 10 mm in diameter (e.g., between a lower value of 0.5 mm, 0.7 mm, 0.8 mm, 0.9 mm, 1 mm, 2 mm, 2.5 mm, 3 mm, 4 mm, 5 mm, 6 mm, 7 mm, 8 mm, 9 mm, 10 mm, etc. and an upper value of 0.7 mm, 0.8 mm, 0.9 mm, 1 mm, 2 mm, 2.5 mm, 3 mm, 4 mm, 5 mm, 6 mm, 7 mm, 8 mm, 9 mm, 10 mm, etc., where the lower value is always less than the upper value).

As mentioned above, the index lip may be used to aid in supporting and guiding the device when cutting into a bony process such as the SP, SAP, IAP, etc. The index lip may aid in setting the device at a predetermined and/or adjustable (as discussed above) offset from the cutter. As mentioned above, the offset may be set or adjusted to between 0.5 mm and 100 mm (preferably between about 1 mm and 10 mm or 2 mm and 10 mm). As also discussed above, the lip may be formed of any appropriate material, including polymers and metals, such as stainless steel, nickel titanium, titanium, aluminum, polypropylene, polyethylene, PEEK, thermoplastics, Teflon, fluoropolymers, composites, etc., including coatings of any of these.

In some variations the index lip may be deformable and/or retractable. For example, the index lip may be deformable and locked into position. The index lip may be indexed off of the top and/or bottom of a bone region to be cut, such as the SAP, IAP, etc.

Figure 29:
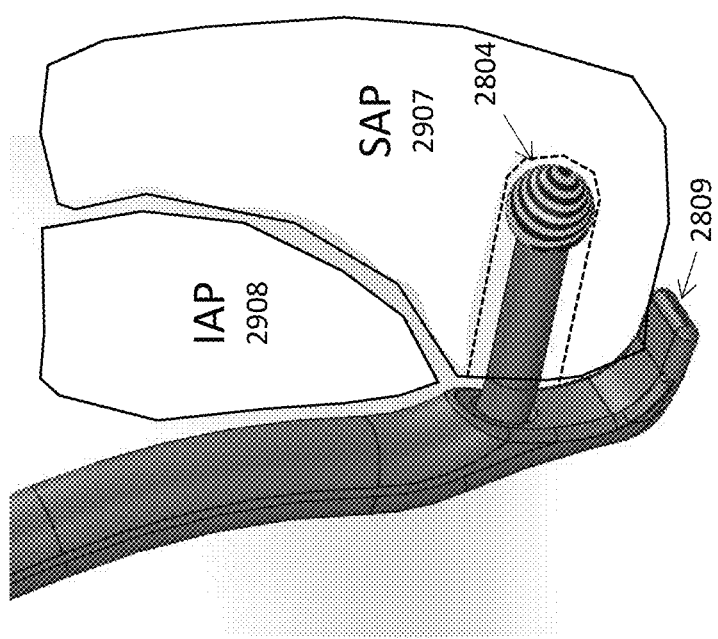
FIG. 29 shows the apparatus of FIGS. 28A and 28B being used to create a medial to lateral through hole in an SAP.

FIG. 29 illustrates one example of a method of cutting bone using an apparatus such as that shown in FIGS. 28A-28B. In this example, the distal end of the device, having an index lip 2809 is positioned (indexed off of) against the underside and/or vertical portion of the facet joint (SAP 2905). In use, a hole may be first drilled into the SAP, as shown, to form a cut and/or channel into the bone. Thus, the drill portion may create a medial to lateral through-hole into the bone. Thereafter, the bone may be cut as discussed above, using a router-like action, shaving caudal to cephalad (or vice versa) to remove bone from this joint. This method of removing bone using the device may be performed in a very controlled manner, and may avoid nearby nerve or neural structures (including the spinal nerve root).

Alternative methods of cutting bone using an apparatus such as the one shown in FIGS. 28A-28B may include a first step of setting the assembly lip 3009 at a specific distance from the drill bit and placing the lip of the device in the SAP 2907, IAP 2908, joint line, or below a portion of the SAP 2907. Next, the apparatus may be used to drill a slot/groove in the SAP and/or IAP structure by sweeping the drill bit back in forth in a caudal-cephalad direction. This can be done in combination with a deployed drill bit to a desired medial-lateral depth in the targeted tissue. Next a user may reduce the lip to drill bit off set distance by continuing to sweep the drill bit caudal to cephalad in a back and forth manner until the drill bit is proximate to the lip. Using this method the targeted bone and ligamentous structures can be shaved away in a step-wise manner while avoiding neural structures (such as the nerve root, spinal cord and cauda equine).

The apparatus shown in FIGS. 28A-28B and any other apparatus in this application may be configured to track the drill bit and/or lip relative to the patient anatomy using an image guidance systems such as the STEATH system by Medtronic or Brain Labs system and optionally in combination with preoperative or intraoperative images generated by flouro machines, MRI, CT machines such as Medtronics O-Arm. The drill bit position can be tracked using inferred reflectors mounted to the cutting tools handle, drill bit plunger element 2711 or other locations. These IR markers and the known dimensions of the cutting tool and its projected path of the drill bit when deployed allows the user to track the drill bit in a virtual manner during the surgical procedure. Alternatively the drill bit or other element of the cutting device can have an integrated electromagnetic coil that would enable tracking of the device in 3D space relative to the patients' anatomy. In addition to the image guidance solution, robotic or robotic-assisted controls may be used to manipulate the cutting tool based on pre-operative or intra-operative images, in combination with the image guidance system. For example, if the user wants to shave off 3 mm of bone from the most ventral position of the SAP and match the existing curvature of the articulating surface of the SAP, the cutting tool may be positioned and deployed in a manner by the robot to remove this appropriate amount of tissue from the patient.

Figure 30B:
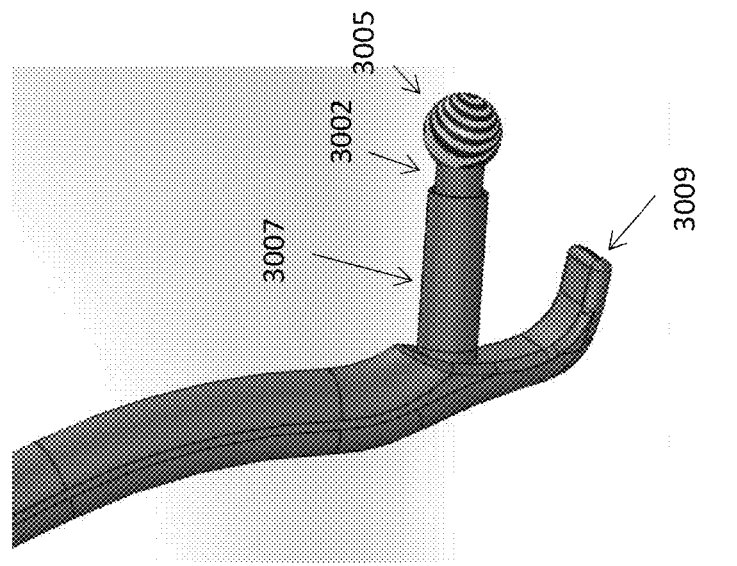
FIGS. 30A and 30B illustrates another example of a deployable rotary device having a telescoping end including a support for a drill bit in a retracted, as shown in FIG. 30A, and an extended, as shown in FIG. 30B, configuration.
Figure 30A:
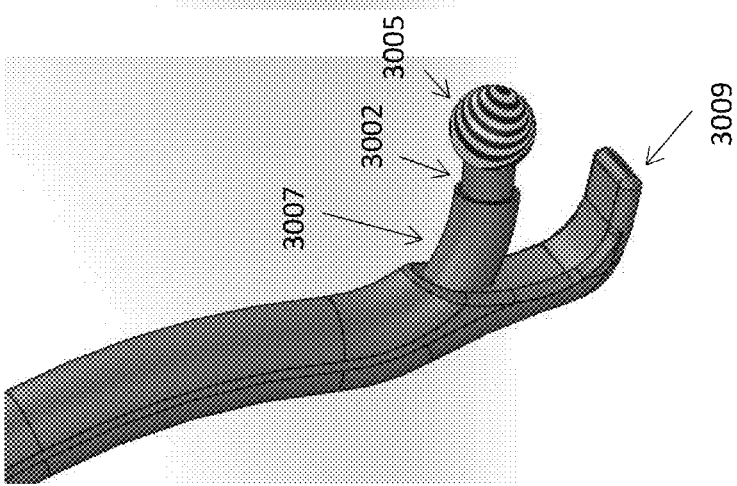

As mentioned above, when cutting the bone to form the medial to lateral through-hole that may be used for later cutting to route/shave off pieces of bone, the devices described herein may include an extending and/or retracting drive shaft (e.g., telescoping drive shaft) for cutting the bone. For example, the apparatus shown in FIGS. 30A-30B illustrates an extendable/retractable drive shaft 3002 for rotating and extending the drill bit 3005, and also includes a telescoping support 3007 surrounding (at least partially) the distal end of the drive shaft. The inner telescoping support 3007 may be a cannula that can be pre-shaped (e.g. particularly when formed of a shape memory material, such as NiTi, cobalt chromium, etc.) and may prevent the drill bit from diverging from its intended path. In some variations, the apparatus may also be configured to include irrigation, e.g., through the inner telescoping support around (and/or within) the drive shaft.

Also described herein are side-cutting devices. Any of the variations described herein may also be used for side cutting, and may be adapted, e.g., by the use of a side-shield for the cutter portion. For example, FIGS. 31A-31C illustrates one variation of a side-cutting apparatus. In this example a shield-cutting shield or support 3103 is included to prevent cutting in the shielded direction. The shield is shown extending from the distal end region of the tool. A cutter (drill bit 3105) is positioned within the shield. Any appropriate drill bit may be used. In FIGS. 31A-31C, the drill bit is configured as a side-cutting (cylindrical) drill bit.

In general, a side-cutting drill bit may be an oscillatory (e.g., back and forth), rotary, and/or vibrational (e.g., ultrasound) cutter. When the cutter (e.g., drill bit) includes cutting channels, ridges, threads, protrusions, etc., these channels, etc. may be circumferential or partially circumferential, lateral, helical, etc., or a textured surface (e.g., diamond, etc.) may be used. The drill bit in any of these embodiments can be made to be clutched on the proximal or distal end of the drive mechanism so the drill bit or cutting element only cuts on hard tissue such as bone or tough ligament rather than compliant and soft neural structures. A side-cutting drill bit may generally have a lateral length, l, 3118 that is greater than its diameter, d. The side-cutting drill may be at least partially retractable within the housing of the distal end of the tool (e.g., the distal end of the intermediate member or cannula) 3102. For example, the length the side-cutting drill bit may be flat (over the majority of its surface, and may extent, for example, between 0.1 and 30 mm (e.g., between a lower limit of about 0.1 mm, 0.2 mm, 0.3 mm, 0.4 mm, 0.5 mm, 0.6 mm, 0.7 mm, 0.8 mm, 0.9 mm, 1 mm, 1.5 mm, 2 mm, 2.5 mm, 3 mm, 3.5 mm, etc. and an upper limit of about 0.2 mm, 0.3 mm, 0.4 mm, 0.5 mm, 0.6 mm, 0.7 mm, 0.8 mm, 0.9 mm, 1 mm, 1.5 mm, 2 mm, 2.5 mm, 3 mm, 3.5 mm, 4 mm, 4.5 mm, 5 mm, 6 mm, 7 mm, 8 mm, 9 mm, 10 mm, 12 mm, 15 mm, 20 mm, 25 mm, 30 mm, etc., where the lower limit is always lower than the upper limit).

The side-cutting shield 3103 may also be configured as a support, and may provide enough stiffness to allow for more precise cutting. The length of the side cutting element may be the same as, greater or less than the length of the drill bit.

In use, a side-cutting tool may be used to perform the second (e.g., cephalad to caudal) cut discussed above. After the medial to lateral drill hole is formed (see, e.g., FIG. 29, as discussed above), a side-cutting device such as the one shown in FIGS. 31A-31C may be inserted using the optional index lip as a guide to help maintain the desired offset.

Figure 32B:
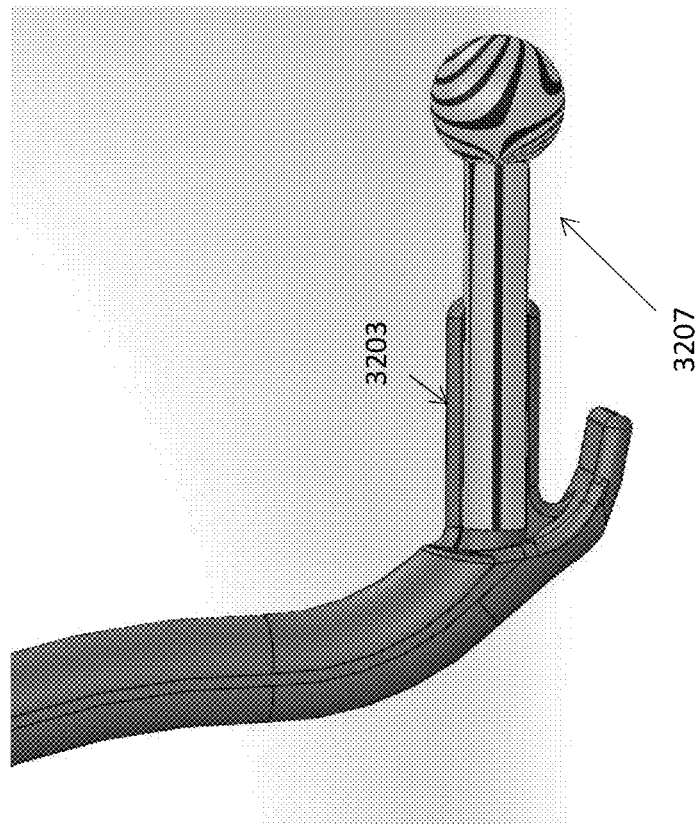
FIGS. 32A and 32B show side views of another variation of a deployable rotary device having side cutting and a telescoping cutter (drill bit) in a retracted (FIG. 32A) and extended (FIG. 32B) configuration.
Figure 32A:
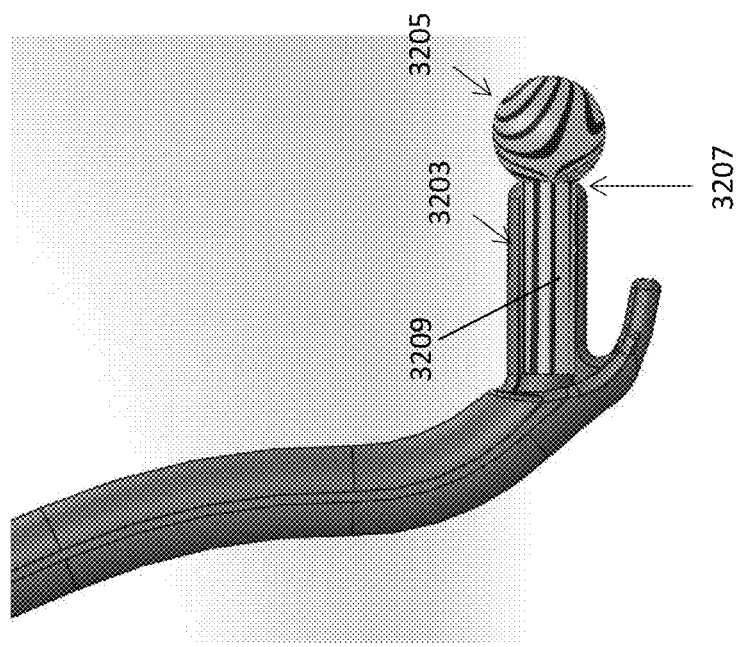

As mentioned above, any of the variations described herein may be adapted as side-cutting devices, and may include a side-cutting shield. In some variations the tool may be combined for both hole drilling (e.g., FIGS. 28A-30B) and side cutting (FIGS. 31A-31B). For example, FIGS. 32A-32B illustrate one variation of an apparatus adapted for both forward, hole-drilling and for side cutting, but including both a side-cutting shield 3203 and side cutting and forward-cutting drill bit 3207. The hybrid drill bit includes, in this example, an enlarged (e.g., spherical, ovoid, etc.) distal end 3205 and a linear/flat profiled side-cutting region (e.g., shown as cylindrical cutter region 3209). The cutter may be (e.g., by pushing/pulling on the drive shaft) extended or retracted from the shield region. In some variations the distal end region of the cutter (ball region 3205 in FIG. 32A) may be housed within a shielded distal portion (not shown), and extended out by pushing the drive shaft. FIG. 32B shows the cutter (drill bit 3207) extended, showing extension from the shield 3203.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the turn does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of cutting and removing a portion of a facet joint which is directly or indirectly impinging on a neural structure, the method comprising:
   drilling a first channel through a cross section of a superior articulating process (SAP) of the facet joint, wherein the first channel is initiated at a medial wall of a joint line between the SAP and an inferior articular process (IAP);
   through the first channel, creating a second channel that is 90 degrees+/−30 degrees relative to the first channel, where the second channel extends from the first channel towards an edge of the SAP to define a portion of the SAP for removal; and
   detaching the portion of the SAP.

2. The method of claim 1, wherein the first channel is initiated from a medial aspect of SAP and extends to a lateral portion of the SAP.

3. The method of claim 1, further comprising placing the facet joint in flexion.

4. The method of claim 1, wherein drilling the first channel through the cross section of the SAP comprises positioning a tool with a lip region that offsets a cutting portion of the tool from an edge of the SAP by a distance of between 1 mm and 15 mm.

5. The method of claim 1, wherein drilling the second channel comprises positioning a tool with a shield around a portion of a cutter.

6. The method of claim 1, wherein a tissue portion is detached from the SAP by breaking or snapping the tissue portion away from the SAP using applied torque, compression, tension and bending moment, creating an additional channel, or any combination thereof.

7. The method of claim 1, wherein the first channel is created by a cutting device which creates a channel along its longitudinal axis, including a curved or straight axis through cutting action near its distal tip.

8. The method of claim 1, wherein the second channel is created by a cutting device, where the second channel is orthogonal to a longitudinal axis of the device.

9. The method of claim 1, where the first and second channels are created by any of the following methods using: a vibrational motion element, rotational motion of an element, longitudinal reciprocation, or any combination thereof.

10. The method of claim 9, wherein vibrational motion is within a frequency range between 1 Hz to 1 MHz.

11. The method of claim 1, wherein the first channel is straight.

12. The method of claim 1, wherein the first channel is curved.

* * * * *